United States Patent [19]
Donati et al.

[11] Patent Number: 5,716,953
[45] Date of Patent: Feb. 10, 1998

[54] 1,5-BENZODIAZEPINE DERIVATIVES

[75] Inventors: Daniele Donati; Antonella Ursini; Mauro Corsi, all of Verona, Italy

[73] Assignee: Glaxo Wellcome S.p.A., Verona, Italy

[21] Appl. No.: 578,535

[22] PCT Filed: Jul. 18, 1994

[86] PCT No.: PCT/EP94/02353

§ 371 Date: Mar. 22, 1996

§ 102(e) Date: Mar. 22, 1996

[87] PCT Pub. No.: WO95/03285

PCT Pub. Date: Feb. 2, 1995

[30] Foreign Application Priority Data

Jul. 20, 1993 [GB] United Kingdom ............ 9314981

[51] Int. Cl.$^6$ ............ A61K 31/55; C07D 243/12
[52] U.S. Cl. ............ 514/221; 540/518
[58] Field of Search ............ 540/518; 514/221

[56] References Cited

FOREIGN PATENT DOCUMENTS

| | | | |
|---|---|---|---|
| A-0 376 849 | 7/1990 | European Pat. Off. | 540/518 |
| A-93 14074 | 7/1993 | WIPO | 540/518 |
| A-93 14075 | 7/1993 | WIPO | 540/518 |
| A-94 13648 | 6/1994 | WIPO | 540/518 |

*Primary Examiner*—Robert T. Bond
*Attorney, Agent, or Firm*—Bacon & Thomas

[57] ABSTRACT

Compounds of formula (I)

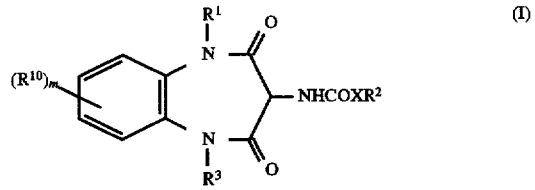

wherein the substituents are defined in the specification are antagonists of gastrin and CCK.

18 Claims, No Drawings

1,5-BENZODIAZEPINE DERIVATIVES

This application is a 371 of PCT/EP94/02353, filed 18 Jul., 1994 which claims priority of GB 9314981.3, filed 20 Jul., 1993.

This invention relates to novel 1,5-benzodiazepine derivatives, to processes for their preparation, to pharmaceutical compositions containing them and to their use in medicine.

Cholecystokinins (CCK) and gastrin are structurally related peptides which exist in gastrointestinal tissue and in the central nervous system. Cholecystokinins include CCK-33, a neuropeptide of thirty-three amino acids in its originally isolated form, its carboxy terminal octapeptide sulphate, CCK-8 (also a naturally-occurring neuropeptide), and 39- and 12-amino acid forms. Gastrin occurs in 34-, 17- and 14- amino acid forms, with the minimum active sequence being the C-terminal tetrapeptide, Trp-Met-Asp-Phe-$NH_2$(CCK-4), which is the common structual element shared by both CCK and gastrin.

CCK and gastrin are gastrointestinal hormones and neurotransmitters in the neural and peripheral systems and perform their respective biological roles by binding to particular receptors located at various sites throughout the body.

There are at least two subtypes of cholecystokinin receptors termed CCK-A and CCK-B and both are found in the periphery and in the central nervous system. CCK and gastrin receptor antagonists have been disclosed for preventing and treating CCK-related and/or gastrin related disorders of the gastrointestinal and central nervous systems of animals, and more particularly humans.

U.S. Pat. No. 4,988,692 describes a group of 3-acylamino 1-alkyl-5-phenyl 1,5-benzodiazepine derivatives as cholecystokinin antagonists. Further the specification teaches that the compounds have a significantly greater affinity for the CCK-A receptor over the CCK-B receptor.

We have now found a novel group of 3-substituted 1,5-benzodiazepine compounds which are potent and specific antagonists of gastrin and/or CCK and in particular antagonists of gastrin and/or CCK at the CCK-B receptor which exhibit a particularly advantageous profile of activity.

Thus, the invention provides compounds of general formula (I)

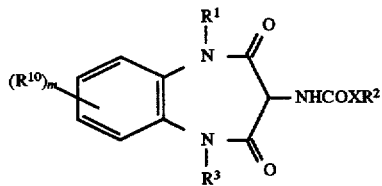

wherein $R^1$ represents a phenyl, $C_{3-7}$cycloalkyl, $C_{7-11}$bridgedcycloalkyl or $C_{1-6}$alkyl group which alkyl group may be substituted by a hydroxy, phenyl, $C_{1-6}$alkoxycarbonyl, $C_{3-7}$cycloalkyl, or $C_{7-11}$bridgedcycloalkyl group;

$R^2$ represents a phenyl group optionally substituted by 1 or 2 substituents selected from, halogen, $C_{1-4}$alkyl, $C_{1-4}$alkylthio, cyano, nitro, trifluoromethyl, trifluoromethoxy, $(CH_2)nR^4$ or $O(CH_2)pR^4$ wherein $R^4$ represents hydroxy, $C_{1-4}$alkoxy, $CO_2R^5$ or $NR^6R^7$; n is zero or 1; p is an integer from 1 to 4;

$R^3$ represents the group AlkNR$^8$R$^9$;

$R^5$ represents hydrogen or $C_{1-4}$alkyl;

$R^6$ represents hydrogen or $C_{1-4}$alkyl;

$R^7$ represents hydrogen, $C_{1-4}$alkyl, acyl, or $C_{2-6}$alkyl substituted by one or more hydroxy, carboxyl and/or amino groups or $R^6$ and $R^7$ together with the nitrogen atom to which they are attached form a 5–7 saturated heterocyclic ring which contain an additional heteroatom selected from oxygen, sulphur or nitrogen and/or may be substituted by 1 or 2 $C_{1-4}$alkyl or hydroxy groups.

$R^8$ and $R^9$ independently represent hydrogen, $C_{1-4}$alkyl or $C_{2-6}$alkyl substituted by one or more hydroxy, carboxyl and/or amino groups or $R^8$ and $R^9$ together with the nitrogen atom to which they are attached represent a 5–7 saturated heterocyclic ring which may contain an additional heteroatom selected from oxygen, sulphur or nitrogen and/or may be substituted by 1 or 2 $C_{1-4}$alkyl or hydroxy groups; Alk represents a straight or branched $C_{2-6}$alkylene chain optionally substituted by an hydroxyl group;

$R^{10}$ represents hydrogen or a halogen atom; m is zero, 1 or 2;

X is oxygen or NH; and pharmaceutically acceptable salts and or metabolically labile esters thereof.

It will be appreciated that compounds of formula (I) possess at least one asymmetric carbon atom (namely the carbon atom occupying the 3-position of the diazepine ring) and the compounds of the invention thus include all stereoisomers and mixtures thereof including the racemates.

In the compounds of formula (I) 'alkyl' when used as a substituent or part of a substituent group means that the group may be straight or branched. Thus, $C_{1-6}$alkyl includes methyl, ethyl, n-propyl, isopropyl, n-butyl, isobutyl or tert-butyl, n-pentyl, isopentyl, neopentyl, n-hexyl, isohexyl, 1,3-dimethylbutyl, 3,3-dimethylbutyl, 2,3-dimethylbutyl.

For the group $R^1$ the term $C_{3-7}$cycloalkyl as a group or part of a group refers to a monocyclic alkyl group such as cyclopropyl, cylobutyl, cyclopentyl, cyclohexyl or cycloheptyl. The term $C_{7-11}$bridged cycloalkyl refers to groups such adamantyl, norbornanyl or norbornenyl.

For the groups $R^5$, $R^6$, $R^7$ $R^8$ and $R^9$ the term $C_{1-4}$alkyl includes 3–4-cycloalkyl (e.g. cyclopropyl or cyclobutyl) as well as straight or branched chain alkyl groups as defined above.

Halogen in the definition of compounds of formula (I) may represent a fluoro, chloro, bromo or iodo substituent.

When $R^2$ is a phenyl group substituted by a single substituent this may be in the ortho, or more preferably the meta or para position.

When the group $R^6$ and $R^7$ together with the nitrogen atom represent a saturated heterocyclic group examples of suitable groups include morpholino, 2,6-dimethylmorpholino, thiomorpholino, piperidino, 4,4-dimethylpiperidino and pyrrolidino.

When $R^6$ and $R^7$ are both alkyl they are conveniently the same e.g. methyl.

When $R^7$ represents acyl this may be for example $C_{1-6}$alkanoyl e.g. formyl or acetyl.

When Alk represents a straight or branched $C_{2-6}$alkylene chain examples of such groups include ethylene, 2-methylethylene, propylene, butylene, pentamethylene or hexamethylene.

When Alk represents a $C_{2-6}$alkylene chain substituted by a hydroxyl group examples of such chains include ethylene or propylene optionally substituted by hydroxymethyl. e.g. 2 hydroxymethyl-ethylene When $R^8$ and $R^9$ together with the nitrogen atom to which they are attached represent an heterocyclic group examples of suitable groups include morpholino, 2,6-dimethylmorpholino, hexamethyleneimino, piperidino, pyrrolidino, piperazino or N-methylpiperazino.

When $R^8$ and $R^9$ independently represent $C_{1-4}$alkyl examples of such groups include methyl or ethyl When $R^{10}$ is halogen this is preferably chlorine or fluorine.

When m is 1 or 2 the halogen atom(s) e.g. chlorine or fluorine are preferably in the 7 and/or 8 positions.

When $R^1$ represents an alkyl group substituted by a hydroxyl group this is preferably a $C_{3-6}$alkyl group substituted by hydroxy. Examples of such groups include 2-hydroxypropyl, 2-hydroxy-3-methylbutyl and 2-hydroxy-3,3-dimethylbutyl of which 2-hydroxy-3-methylbutyl, and 2-hydroxy-3,3-dimethylbutyl are particularly preferred.

When $R^1$ represent an alkyl group substituted by a $C_{3-7}$cycloalkyl group this is preferably a $C_{1-3}$alkyl group such as methyl, ethyl or 1-methylethyl, substituted by a $C_{3-7}$cycloalkyl group such as cyclopentyl, or cyclohexyl.

When $R^1$ is a bridged $C_{7-11}$cycloalkyl group this may be for example an adamantyl group such as 1-adamantyl or 2-adamantyl group or a 2-norbornanyl group.

When $R^1$ is an alkyl group substituted by a bridged $C_{7-11}$cycloalkyl group this is preferably an ethyl group or more especially a methyl group substituted by a bridged $C_{7-11}$cycloalkyl group. Examples of suitable bridged cycloalkyl groups include adamantyl such as 1-adamantyl or 2-adamantyl, 2-norbornanyl or 5-norbornenyl. Most preferably $R^1$ represents 1-adamantylmethyl.

When $R^1$ is alkyl substituted by phenyl this may be for example benzyl or phenethyl.

When $R^1$ is alkyl substituted by alkoxycarbonyl this is preferably methyl substituted by alkoxycarbonyl such as methoxycarbonyl or as t-butoxycarbonyl.

Examples of suitable $R^1$ groups include a phenyl, adamantyl, norbornanyl, phenethyl, $C_{4-6}$alkyl e.g. n-butyl, 3-methyl butyl, 3,3-dimethyl butyl, 1,3-dimethylbutyl, 2,3-dimethylbutyl, $C_{3-6}$hydroxy alkyl e.g. 2-hydroxypropyl, 2-hydroxy-3- methylbutyl, 2-hydroxy-3,3-dimethylbutyl, $C_{1-2}$alkyl substituted by a bridged $C_{7-10}$cycloalkyl group e.g. 2-norbornanylmethyl, 5-norbornenylmethyl, 2-adamantylmethyl, 2-adamantylethyl, 2-(1-adamantyl) ethyl, 1-adamantylmethyl, alkoxycarbonylalkyl, e.g. methoxycarbonylmethyl or t-butyoxycarbonylmethyl, cyclohexylmethyl, or 2-cyclopentylethyl.

Conveniently $R^1$ represents phenyl, cyclohexylmethyl, 3-methylbutyl or 1-adamantylmethyl and more particularly 3-methylbutyl or 1-adamantylmethyl.

Examples of suitable $R^2$ groups include phenyl or phenyl substituted by one or two groups selected from fluorine, chlorine, bromine, methyl, methoxy, hydroxy, trifluoromethyl or thiomethyl.

Conveniently $R^2$ is a phenyl group or a phenyl group substituted in the meta or para position by a single substituent selected from fluorine, chlorine, bromine methyl, methoxy, hydroxy, trifluoromethyl or methylthio.

Preferably $R^2$ represents phenyl, 3-methylphenyl, 4-fluorophenyl, 4-methoxyphenyl or more especially phenyl.

Conveniently the group X represents NH

Conveniently the group Alk represents ethylene, propylene or 2-hydroxymethylethylene.

Conveniently the group $NR^8R^9$ represents amino, dimethylamino, diethylamino, morpholino, pyrrolidino, piperidino or hexamethyleneimino.

$R^{10}$ conveniently represents fluorine or chlorine or more particularly hydrogen.

Examples of suitable $R^3$ groups include morpholinoethyl, pyrrolidinoethyl, piperidinoethyl, dimethylaminoethyl, diethylaminoethyl, dimethylaminopropyl, amino-propyl, 2-hydroxymethyl-2-aminoethyl or hexamethyleneiminoethyl.

Conveniently $R^3$ represents morpholinoethyl, piperidinoethyl, pyrrolidinoethyl, dimethylaminoethyl, diethylaminoethyl, dimethylamino-propyl or 2-hydroxymethyl-2-aminoethyl or hexamethyleneiminoethyl Preferably $R^3$ represents morpholinoethyl.

Examples of suitable compounds of formula (I) are those wherein $R^1$ represents 1-adamantylmethyl and $R^3$ represents morpholinoethyl, X represents NH and, $R^{10}$ represents hydrogen A preferred group of compounds of formula (I) include those wherein $R^1$ is 1-adamantylmethyl, $R^2$ is phenyl optionally substituted by halogen e.g. fluorine or bromine, $R^3$ represents, 2-(4-morpholino)ethyl, 2-(1-piperidino)ethyl, 2-(1-pyrrolidino)ethyl, 2-(dimethylamino)ethyl, 3-(dimethylamino)propyl, 2-hydroxymethyl-2-aminoethyl, 3-aminopropyl, X is NH and $R^{10}$ is hydrogen or fluorine and m is 1.

A further preferred group of compounds of formula (I) include those wherein $R^1$ is 3-methylbutyl, $R^2$ is phenyl optionally substituted by methyl, methoxy, chlorine, bromine, fluorine, trifluoromethyl, hydroxy or methoxy, $R^3$ is 2-(dimethylamino)ethyl, 2-(diethylamino)ethyl, 2-(1-piperidino)ethyl or 2-(4-morpholino)ethyl. X is NH, $R^{10}$ is hydrogen or fluorine and m is 1.

Compounds wherein $R^1$ is cyclohexylmethyl, $R^2$ is phenyl or 3-methylphenyl $R^3$ is 2-(diethylamino)ethyl or 2-(4-morpholino)ethyl, X is NH and $R^{10}$ is hydrogen represent a further preferred group of compounds of this invention. Another preferred group of compounds according to the invention include those wherein $R^1$ is phenyl, $R^2$ is phenyl optionally substituted by methyl, fluoro or 3-methylthio, $R^3$ is 2-(1-hexamethylenimino)ethyl, X is NH and $R_{10}$ is hydrogen.

Preferred compounds of the invention include:

N-[1-(1-Adamantylmethyl)-2,4-dioxo-5-[2-(4-morpholino) ethyl]-2,3,4,5-tetrahydro-1H-benzodiazepin-3-yl]-N'-phenylurea;

N-[1-(1-Adamantylmethyl)2,4-dioxo-5-[2-(4-morpholino) ethyl]-2,3,4,5 tetrahydro-1H-benzodiazepin-3-yl]-N¹-(4-fluorophenyl) urea.

N-[2,4-Dioxo-1-(3-methyl-1-butyl)-5-[2-(4-morpholino) ethyl]-2,3,4,5-tetrahydro-1H-1,5-benzodiazepin-3-yl]-N'-phenylurea;

N-[2,4-Dioxo-1-(3-methyl-1-butyl)-5-[2-(1-piperidino) ethyl]-2,3,4,5-tetrahydro-1H-1,5-benzodiazepin-3-yl]-N'-phenylurea;

N-[5-[2-(Dimethylamino)ethyl]-2,4-dioxo-1-(3-methyl-1-butyl) -2,3,4,5-tetrahydro-1H-1,5-benzodiazepin-3-yl]-N'-phenylurea;

N-[5-[2-(Dimethylamino)ethyl]-2,4-dioxo-1-(3-methyl-1-butyl) -2,3,4,5-tetrahydro-1H-1,5-benzodiazepin-3-yl]-N'-(4-methoxyphenyl)urea N-[2,4-Dioxo-1-(3-methyl-1-butyl)-5-[2-(4-morpholino) ethyl]-2,3,4,5-tetrahydro-1H-1,5-benzodiazepin-3-yl]-N'-(4-methoxyphenyl)urea;

N-[2,4-Dioxo-1-(3-methyl-1-butyl)-5-[2-(4-morpholino) ethyl]-2,3,4,5-tetrahydro-1H-1,5-benzodiazepin-3-yl]-N'-(4-hydoxyphenyl)urea;

N-[5-[2-(diethylamino)ethyl]-2,4-dioxo-1-(3-methyl-1-butyl)-]-2,3,4,5-tetrahydro-1H-benzodiazepin-3-yl]-N'-phenylurea;

N-[5-[2-diethylamino)ethyl]-2,4-dioxo-1-(3-methyl-1-butyl)-]-2,3,4,5-tetrahydro-1H-benzodiazepin-3-yl]-N'-N'-(4-fluorophenyl)urea;;

N-[(1-Adamantylmethyl)-5-[2-(dimethylamino)ethyl]-2,4-dioxo-2,3,4,5-tetrahydro-1H-1,5-benzodiazepin-3-yl]-N'-phenylurea;

N-[1-(1-Adamantyl)methyl-5-[3-(dimethylamino)propyl]-2,4-dioxo-2,3,4,5-tetrahydro-1H-1,5-benzodiazepin-3-yl]-N'-phenylurea;

N-[1-(1-Adamantylmethyl)-2,4-dioxo-5-[3-hydroxy-2(R) aminopropyl]-2,3,4,5-tetrahydro-1H-1,5-benzodiazepin-3-yl]-N'-phenylurea hydrochloride;

N-[1-(1-Cyclohexylmethyl-2,4-dioxo -5-[2-(diethylamino) ethyl]-2,3,4,5-tetrahydro-1H-benzodiazepin-1H-benzodiazepin-3-yl]-N'-phenylurea;

N-[1-(1-Adamantylmethyl)-2,4-dioxo-7-fluoro-5-[2-(4-morpholino)-ethyl]-2,3,4,5-tetrahydro-1H-1,5-benzodiazepin-3-yl]-N'-phenylurea;

N-[1-(3-methyl-1-butyl)]-2,4-dioxo-5-(2-(4-morpholino) ethyl)]-2,3,4,5-tetrahydro-1H-benzodiazepin-3-yl]-N'-(4-chlorophenyl)urea;

N-[2,4-Dioxo-1-(3-methylbut-1-yl)-5-[2-(4-morpholino) ethyl]-2,3,4,5-tetrahydro-1H-1,5-benzodiazepin-3-yl]-N'-(4-trifluoromethyl)phenylurea;

N-[1-(1-Adamantyl methyl)-2,4-dioxo-5-[2-(1-pyrrolidino) ethyl]-2,3,4,5-tetrahydro-1H-benzodiazepin-3-yl]-N'-phenylurea N-[2,4-Dioxo-1-[2-(hexamethyleneimino)ethyl]-5-phenyl-2,3,4,5-tetrahydro-1H-benzodiazepin-3-yl]-N'-(3-tolyl) urea;

and enantiomers and physiologically acceptable salts thereof.

A particularly preferred compound of the invention is (−)[1-(1-Adamantylmethyl)]-2,4-dioxo-5-[2-(N-morpholino)-ethyl]-2,3,4,5-tetrahydro-1H-1,5-benzodiazepin-3-yl)-N'-phenylurea and physiologically acceptable salts thereof.

The pharmaceutically acceptable salts of the compounds of formula (I) include conventional salts formed for example from pharmaceutically acceptable inorganic or organic acids as well as quaternary ammonium acid addition salts. Examples of suitable salts include hydrochloric, hydrobromic, sulphuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts.

The compounds of formula (I) in which $R^5$ represents hydrogen may form pharmaceutically acceptable salts with suitable cations. Suitable pharmaceutically acceptable cations include alkali metal (e.g. sodium or potassium) and alkaline earth metal (e.g. calcium or magnesium) cations.

Salts may also be formed with organic bases e.g. N-methylglucamine. The invention also includes metabolically labile esters of compounds of formula (I) wherein $R^5$ represents hydrogen. Examples of such metabolically labile esters include $C_{1-4}$alkyl esters e.g. methyl or ethyl esters, substituted or unsubstituted aminoalkyl esters (e.g. aminoethyl, 2-(N,N-diethylamino) ethyl, or 2-(4-morpholino)ethyl esters) or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-methoxy-1-methyl-ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxycarbonyloxyethyl) or 1-(4-tetrahydropyranylcarbonyloxy)ethyl.

The compound of formula (i) and salts and metabolically labile esters thereof may form solvates e.g. hydrates and the invention includes such solvates.

The compounds of the invention are potent and specific antagonists of gastrin and/or CCK and in particular gastrin and or CCK at the CCK-B-receptor. Thus compounds of the invention have been shown to be antagonists of CCK, particularly at CCK-B receptors as demonstrated for example by the compound's ability to inhibit the contractile actions of CCK-4 in the presence of a CCK-A antagonist, in the guinea-pig isolated ileum longitudinal muscle-myenteric plexus.

Compounds of the invention have also been found to have a significantly weaker activity at CCK-A receptors compared with their activity at gastrin and/or CCK-B receptors, as demonstrated by their ability to inhibit the contractile activity of CCK-8 in guinea-pig isolated ileum longitudinal muscle-myenteric plexus.

The preparation and use of guinea-pig isolated ileum longitudinal muscle-myenteric plexus has been described by K-H Buchheit et al in Nauyn-Schmeideberg's Arch. Pharmacol. (1985), 329, p 36–41 and by V. L. Lucaites et al (1991) in J. Pharmacol. Exp. Ther., 256, 695–703.

The compounds of the invention have also been shown to be antagonists of gastrin as demonstrated by their ability to inhibit pentagastrin-stimulated acid secretion from rat isolated gastric mucosa using the procedure described by J. J. Reeves and R. Stables in Br. J. Pharmac., 1985, 86, p.677–684.

The greater affinity of the compounds of the invention for the CCK-B receptor over the CCK-A receptor has also been established using the CCK receptor binding assays described by G Dal Forno et al., J. Pharmcol. Exp & Ther. 261, 1056–1063, 1992.

The compounds of the invention are therefore useful for the treatment and/or prevention of disorders in mammals, especially humans, where modification of the effects of gastrin or CCK is of therapeutic benefit. Thus the compounds of the invention are useful for the treatment of central nervous system disorders where CCK and/or gastrin are involved. For example anxiety disorders (including panic disorder, agoraphobia, social phobia, simple phobia, obsessive compulsive disorders, post traumatic stress disorder, and general anxiety disorder), tardive dyskinesia, depression, Parkinson's disease or psychosis. The compounds of the invention are also useful for the treatment of gastrointestinal disorders especially those where theta is an advantage in lowering gastric acidity. Such disorders include peptic ulceration, reflux oesophagitis and Zollinger Ellison syndrome. They may also be useful for the treatment of gastrointestinal disorders such as irritable bowel syndrome, excess pancreatic secretion, acute pancreatitis, motility disorders, antral G cell hyperplasia, fundic mucosal hyperplasia or gastrointestinal neoplasms. They may also be useful for the treatment of dependency on drugs or substances of abuse and withdrawal, Gilles de la Tourette syndrome, or dysfunction of appetite regulatory systems; as well as the treatment of certain tumours of the lung, lower oesophagus, pancreas, stomach, intestines and colon. Compounds of the invention are also useful for directly inducing analgesia, or enhancing opiate or non-opiate mediated analgesia, as well as anaesthesia or loss of the sensation of pain.

Compounds of the invention have also been found to exhibit anxiolytic activity in conventional pharmacological tests. For example in mice in the black-white box test and marmoset threat test.

The invention therefore provides a compound of formula (I) or a pharmaceutically acceptable salt or solvate thereof for use in therapy, in particular in human medicine.

According to another aspect the invention provides the use of a compound of formula (I) or a pharmaceutically acceptable salt or solvate thereof for the manufacture of a medicament for the treatment of conditions where modification of the effects of gastrin and/or CCK is of therapeutic benefit.

According to a further aspect of the invention we provide a method for the treatment of a mammal, including man, in particular in the treatment of conditions where modification of the effects of gastrin and/or CCK is of therapeutic benefit which method comprises administering an effective amount of a compound of formula (I) or a pharmaceutically acceptable salt or solvate thereof to the patient.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated and the age and the condition of the patient and will be ultimately at the discretion of the attendant physician or veterinarian. In general however doses employed for adult human treatment will typically be in the range of 0.01–2000 mg per day e.g 0.01–500 mg per day.

The desired dose may conveniently be presented in a single dose or as divided doses administered at appropriate intervals, for example as two, three, four or more sub-doses per day.

Because the compounds of the invention antagonise the function of CCK in animals, they may also be used as feed additives to increase the food intake in animals in daily dosages of around 1 mg/kg to 10 mg/kg.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, or rectal administration. Oral administration is preferred.

Tablets and capsules for oral administration may contain conventional excipients such as binding agents, for example, syrup, accacia, gelatin, sorbitol, tragacanth, hydroxypropyl cellulose, mucilage of starch or polyvinylpyrrolidone; fillers, for example, lactose, sugar, microcrystalline cellulose, maize-starch, calcium phosphate or sorbitol; lubricants, for example, hydrogenated vegetable oils, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as oral drops or a dry product for constitution with water or other suitable vehicle before use. Such preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in prefilled syringes, vials and ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form which may be obtained by freeze drying for constitution with a suitable vehicle, e.g. sterile, pyrogen-free water, before use.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups $R^1$–$R^{10}$ are as defined for the compounds of formula (I) unless otherwise stated.

According to a first general process (A) compounds of formula (I) wherein X is NH may be prepared by reacting a compound of formula (II) in which Y represents the group NHCOR$^{11}$ wherein R$^{11}$ is an optionally substituted phenoxy group or a 1-imidazole group.

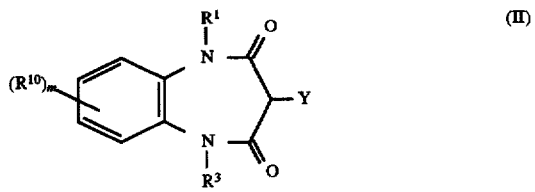

(II)

with an amine of formula (III)

$H_2NR^2$ (III)

optionally in the presence of a base such as a tertiary amine (e.g. triethylamine). The reaction conveniently takes place in a suitable solvent such as a halogenated hydrocarbon (e.g. dichloromethane) or an ether (e.g. tetrahydrofuran) or an amide e.g. N,N-dimethylformamide optionally at a temperature ranging from room temperature to the reflux temperature of the solvent.

In a particular aspect of the process (A) when Y is the group $NHCOR^{11}$ and $R^{11}$ is a 1-imidazole group, the imidazolide (II) may be formed in situ in which case the amine of formula (III) will be mixed with a compound of formula (IV)

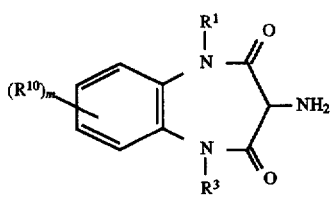

in the presence of carbonyldiimidazole under the aforementioned conditions. For process A when Y is the group $NHCOR^{11}$ and $R^{11}$ is optionally substituted phenoxy group the reaction with the primary amine (III) is preferably carried out in the presence of a base such as a tertiary amine e.g. triethylamine.

The compounds of formula (II) wherein $R^{11}$ is an optionally substituted phenoxy group may be prepared from the primary amine (IV) by reaction with the corresponding optionally substituted phenyl chloroformate in the presence of a base such as pyridine. The reaction may be carried out in a solvent such as a halohydrocarbon e.g. dichloromethane and at a temperature from 0°–50°.

Compounds of formula (II) wherein $R^{11}$ is a 1-imidazole group may be prepared by reacting a compound of formula (IV) with carbonyldiimidazole in the presence of a suitable solvent such as a halogenated hydrocarbon (e.g. dichloromethane) or an ether (e.g. tetrahydrofuran) at a temperature ranging from 0° to 80° (conveniently at room temperature).

According to a further general process (B) compounds of formula (I) may be prepared by reacting a compound of formula (IV) with an isocyanate of formula (V)

$$O=C=N-R^2 \qquad (V)$$

or an acyl chloride of formula (VI)

$$ClCO(X)R^2 \qquad (VI)$$

The reaction conveniently takes place in the presence of a suitable solvent such as a halohydrocarbon (e.g. dichloromethane), an ether (e.g tetrahydrofuran) or a nitrile (e.g. acetonitrile) or a mixture thereof at a temperature in the range of 0° C. to 80° C.

Compounds of formula (IV) may be prepared by reduction of compounds of formula (VII)

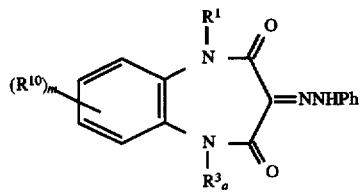

wherein $R^3_a$ represents the group $R^3$ as defined in formula (I)

Compounds of formula (VII) may be reduced to a compound of formula (IV) by reaction with zinc and acetic acid. This reaction may be carried out a temperature with the range 0°–50°. Alternatively the reduction may be carried out using palladium on charcoal and ammonium formate in a solvent such as methanol.

Compounds of formula (VII) may be prepared by reaction of the ortho-phenylenediamine (VIII) with the diacid chloride (IX), in a suitable solvent such as an ether e.g. tetrahydrofuran or an ester e.g. ethyl acetate.

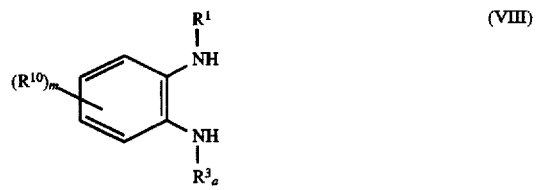

Compounds of formula (VIII) are either known compounds or may be prepared by analogous methods. Thus for example a compound of formula (VIII) may be prepared by alkylation of the amine (X).

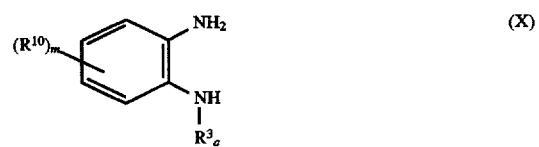

Thus the amine (X) may be reacted with the compound $R^1L$, in which L is a leaving group e.g. chlorine or bromine, optionally in the presence of sodium iodide in a solvent such as N,N-dimethylformamide. Alternatively the group $R^1$ may be introduced wherein the amine (X) is reacted with an appropriate aldehyde under standard reductive alkylation conditions.

In general, the compounds of formula (III), V and (VI) are either known compounds or may be prepared according to methods used for the preparation of known compounds.

According to a further process (C) a compound of formula (I) may be prepared by reaction of a compound of formula (XI)

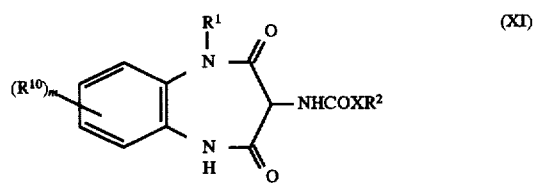

with reaction with the alkylating agent $R^8R^9N$ Alk L wherein L is a leaving group e.g. a halogen. This process is conveniently carried out in the presence of a strong base such as an alkali metal carbonate e.g. potassium carbonate or sodium hydride and in an aprotic solvent such as NN-dimethyl formamide.

The compounds of formula (XI) may be prepared from the amine (XII) wherein $R^1$, $R^{10}$ and m have the meanings defined on formula (I) and $R^3_a$ is a hydrogen atom or a nitrogen protecting group.

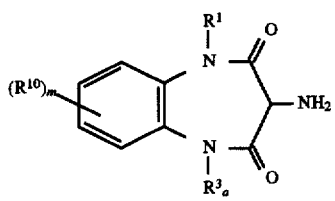

(XII)

by reaction with the isocyanate (V) or the acid chloride (VI) under the conditions described above for the preparation of the compounds of formula (I) from the amine (IV), followed if necessary by removal of the nitrogen protecting group $R^3_a$.

Compounds of formula (XII) may be prepared from compounds of formula (VII) wherein $R^3_a$ is nitrogen protecting group e.g. benzyl or p-methoxybenzyl group. Thus the compound of formula (VII) may be reduced with palladium on charcoal in the presence of ammonium formate to give the required compound of formula (XII) wherein $R^3_a$ represents a hydrogen atom. Alternatively the required compound of formula (XII) may be prepared by reduction of the compound of formula (VII) wherein $R^3_a$ is a nitrogen protecting group followed if desired by the subsequent removal of the said $R^3_a$ nitrogen protecting group using conventional procedures. Thus the reduction of the hydrazone may be affected using zinc and acetic acid and if desired, the nitrogen protecting group subsequently removed by hydrogenolysis or reaction with ceric ammonium nitrate.

The amines of formula (VIII wherein $R^3_a$ is hydrogen) or formula (XI) are either known compounds or may be prepared from the corresponding nitro derivatives (XIII) or (XIV)

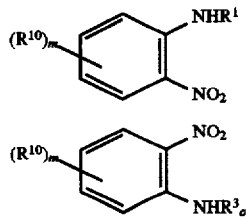

(XIII)

(XIV)

Reaction of the nitro compounds (XIII) or (XIV) with $Na_2S_2O_4$ yields the corresponding primary amine which can then be alkylated in a conventional manner to give the required diamine (VIII).

The compounds of formula (XII) wherein $R^3_a$ is hydrogen may be prepared from the compounds of formula (XV)

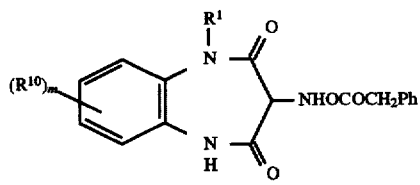

(XV)

by removal of the N-benzyloxycarbonyl protecting group using standard procedures e.g. hydrogenolysis with hydrogen and a palladium catalyst.

The compounds of formula (XV) may be prepared by treating the compound (XVI)

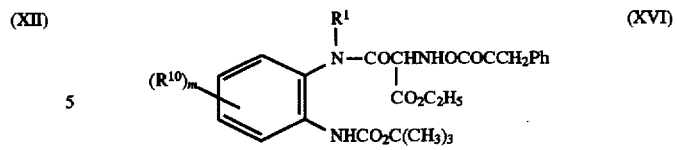

(XVI)

with a suitable acid e.g. hydrochloric acid.

The compound of formula (XVI) may be prepared by reaction of the protected diamine (XVII)

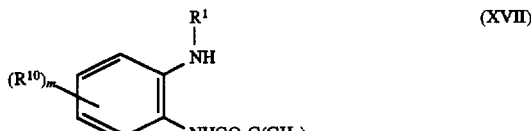

(XVII)

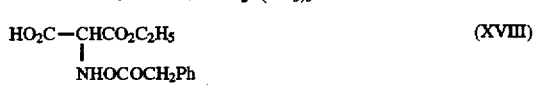

(XVIII)

with the acid (XVIII) in the presence of dicyclohexylcarbodiimide.

The protected diamine (XVII) may be prepared from the corresponding nitro derivative (XIII) by standard procedures. Thus the nitro group may be reduced by reaction with $Na_2S_2O_4$ and the resultant amine converted into the corresponding N-t-butoxycarboxy derivative by standard procedures.

According to a further process (D) compounds of formula (I) may be prepared by reaction of a compound of formula (XIX), wherein $R^1$, $R^2$, $R^{10}$, m and alk have the meanings defined in formula (I) and L is a leaving group

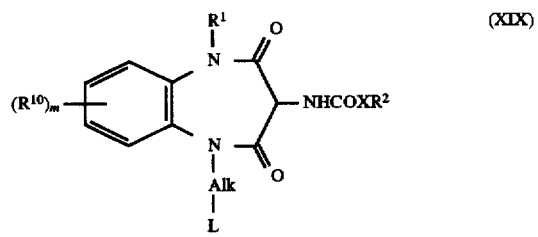

(XIX)

with an amine $R^8_a R^9_b$ NH wherein $R^8_a$ and or $R^9_b$ NH wherein $R^8_a$ and or $R^9 b$, have the meanings defined for the groups $R^8$ and $R^9$ respectively or each may independently represent a nitrogen protecting group such as an arylmethyl group e.g. benzyl, or p-methoxybenzyl, followed where necessary or desired by removal of any said nitrogen protecting group. The reaction may be carried out in the absence or presence of and additional solvent e.g. an ether such as tetrahydrofuran. Conveniently the leaving group L is a halogen atom of e.g. chlorine bromine or iodine, or sulphonyloxy such as alkylsulphonyloxy e.g. methanesulphonyloxy or arylsulphonyloxy e.g. phenylsulphonyloxy. The nitrogen protecting group $R^8_a$ or $R^9_b$ may be removed by conventional procedures e.g. hydrogenolysis.

The compounds of formula (XIX) may be prepared from the corresponding compound of formula (XIX) wherein L represents an hydroxyl group using conventional procedures. Thus compounds of formula (XIX) wherein L is a sulphonyloxy group may be prepared by reaction of the corresponding hydroxy compound with the appropriate alkyl or aryl sulphonylchloride in the presence of a tertiary organic base.

Compounds of formula (XIX) wherein L is a halogen atom may be prepared from the corresponding hydroxy compound using standard procedures for converting hydroxyl groups into halo derivatives. Thus for example compounds of formula (XIX) wherein L is bromine may be prepared by treatment of the corresponding hydroxyl compound with carbon tetrabromide and triphenyl phosphine.

Compounds of formula (XIX) wherein L is hydroxy may be prepared from the corresponding amine (VIII) wherein $R^3a$ is a protected hydroxyalkyl group by reaction with the diacid chloride (IX) followed by reduction of the hydrazone thus formed to give the amine (XII) wherein $R^3a$ is an hydroxyalkyl group or a protected derivative thereof.

Reaction of the resultant amine (XII) with the isocyanate (V) or acyl chloride (VI) yields the desired compound XIX wherein L is an hydroxyl group.

According to a further process (E) a compound of formula (I) may be converted into another compound of formula (I) using conventional techniques.

Thus compounds of formula (I) wherein $R^2$ is phenyl substituted by hydroxy may be prepared from compounds wherein $R^2$ is phenyl substituted by methoxy by conventional means e.g. reaction with aluminium iodide. Similarly compounds of formula (I) wherein $R^2$ is a phenyl group substituted by a carboxyl group may be prepared by hydrolysis of the corresponding compound of formula (I) wherein $R^2$ is a phenyl group substituted by an alkoxycarbonyl group.

In the processes described above the groups $R^1$, $R^2$ and $R^3$ in the intermediates II, III, V and VI may be a group as defined in formula (I) or a group convertible thereto.

The metabolically labile esters of the compounds of formula (I) may be prepared from the corresponding carboxylic and by conventional means. Acid addition salts of compounds of formula (I) may be prepared by conventional means. Thus for example a compound of formula (I) may be treated with the desired acid, conveniently in the presence of a solvent, e.g. an alkanol to give a solution of the required salt which may then be isolated in a conventional manner.

Compounds of formula (I) contain at least one asymmetric carbon atom, namely the carbon atom of the diazepine ring to which the grouping $NHCOXR^2$ is attached. Specific enantiomers of the compounds of formula (I) may be obtained by resolution of the racemic compound using conventional procedures such as chiral HPLC. Alternatively the specific enantiomers of formula (I) may be prepared from the appropriate enantiomer of the compounds of formula (IV) using the processes described above for preparing compounds as the invention from the compounds of formula (IV)

The specific enantiomers of the compound of formula (IV) may be prepared by conventional procedures. Thus the racemic amine (IV) may be reacted with an optically active reagent such as a derivative of phenylalanine or Mandelic acid and the resultant diastereoisomers may be separated by conventional procedures. The required enantiomeric amine (IV) may then be obtained from the single diastereoisomer by removal of the phenylanine or mandelic acid residue by conventional procedures.

The following examples, which are non-limiting, illustrate the invention.

In the Preparations and Examples, unless otherwise stated: Melting points (m.p.) were determined on a Buchi m.p. apparatus and are uncorrected. All 0temperatures refer to 0C. Infrared spectra were measured in chloroform-$d_1$ solutions on a FT-IR instrument. Proton Magnetic Resonance (1H-NMR) spectra were recorded at 300 MHz as solutions in chloroform-$d_1$. Chemical shifts are reported in ppm downfield (d) from Me4Si as an internal standard, and are assigned as singlets (s), doublets (d), doublet of doublets (dd) or multiplets (m). Column chromatography was carried out over silica gel (Merck AG Darmstadt, Germany). Solutions were dried over anhydrous sodium sulphate. "Petrol" refers to petroleum ether, b.p.40°–60° C. Dichloromethane was redistilled over calcium hydride; tetrahydrofuran was redistilled over sodium; ethyl ether was redistilled over sodium and ethyl acetate was dried over activated molecular sieves. The following abbreviations are used in the text. EA=ethyl acetate, CH=cyclohexane, P=petroleum ether 40°–60° C., THF=tetrahydrofuran, DCM=dichloromethane, EE=ethyl ether, DMF=N,N-dimethylformamide. Tlc refers to thin layer chromatography on silica plates. All the compounds are intended as racemic mixtures unless otherwise indicated.

Intermediate 1

N-(4-Methoxyphenylmethyl)-2-nitroaniline

A mixture of 1-fluoro-2-nitrobenzene (20 g) and 4-methoxybenzylamine (18.52 ml) in dry tetrahydrofuran (100 ml) was stirred at 23° for 18 h under a nitrogen atmosphere. The mixture was filtered, then the organic layer was concentrated in vacuo to an oil. Ethanol (50 ml) was added and a solid separated. After filtration, the title compound was obtained as an orange solid (16.35 g). The filtrate was concentrated in vacuo and the residue was treated with further ethanol (10 ml) to give a further amount of title compound (7.9 g). M.p. 81°–2° T.l.c. CH-EA (8:2), $R_f$ 0.55.

Intermediate 2

N-(4-Methoxyphenylmethyl)-1,2-phenylenediamine

Potassium carbonate (96.95 g) and sodium hydrosulfite (80.96 g) were added to a suspension of the intermediate 1 (24 g) in 95% ethanol (500 ml) and water (500 ml). The mixture was stirred at 23° for 1 h, then acidified with conc. hydrochloric acid (150 ml) until pH=3. The mixture was concentrated in vacuo to half volume and the residue was basified with a 10% sodium hydroxide solution (900 ml) until pH=10. The mixture was extracted with ethyl acetate (1200 ml). The organic layer was washed with brine (600 ml), dried, and concentrated in vacuo to a brown solid. This material was triturated with diethyl ether to give the title compound as a beige solid (17.7 g). M.p.91°–2° T.l.c. CH-EA (8:2), $R_f$ 0.22.

Intermediate 3

N-(4-Methoxyphenylmethyl)-N'-(3-methyl-1-butyl)-1,2-phenylenediamine

Bromo 3-methylbutane (10.68 ml) was added to a solution of intermediate 2 (19.5 g) and sodium iodide (12.8 g) in dimethylformamide (400 ml) under a nitrogen atmosphere. The solution was heated to 80° for 4 h under a nitrogen atmosphere, then cooled to room temperature, diluted with water (300 ml) and extracted with diethyl ether (2×700 ml). The combined organic extracts were washed with brine (1000 ml), dried and concentrated in vacuo to an oil, which was purified by flash chromatography (eluting with CH-EA 9:1) to give the title compound as a yellow oil (14.0 g). T.l.c. CH-EA (9:1), $R_f$ 0.42. IR: 1610 and 1601 (C=C) $cm^{-1}$; 1H-NMR :7.31 (d); 6.89 (d); 6.84-6.74 (m); 4.22 (s); 3.81 (s); 3.10 (t); 1.75 (m); 1.6-1.5 (m); 0.94 (d).

Intermediate 4

2,4-Dioxo-5-(4-methoxyphenylmethyl)-1-(3-methyl-1-butyl)-3-phenylhydrazono-2,3,4,5-tetrahydro-1H-1,5-benzodiazepine Intermediate 3 (14.0 g) and 2-phenylhydrazonomalonyldichloride (13.8 g) were each taken up in THF (100 ml) and dropped in a flask containing THF (100 ml) under a nitrogen atmosphere. After complete addition, the solution was heated at 50° for 2 h. The solution was concentrated in vacuo and the residue was triturated with diethyl ether to give the title compound as a yellow solid (8.9 g). The filtrate was concentrated in vacuo and purified by flash chromatography (eluting with CH-EA 8:2) to give a further amount of title compound (6.35 g). M.p.189°–191° T.l.c. CH-EA (8:2), $R_f$ 0.30.

Intermediate 5

3-Amino-2,4-dioxo-5-(4-methoxyphenylmethyl)-1-(3-methyl-1-butyl) -2,3,4,5-tetrahydro-1H-1,5-benzodiazepine Zinc dust (15.8 g) was added to a suspension of the intermediate 4(15.25 g) in acetic acid (150 ml). The mixture was heated at 400 for 2 h, then decanted from zinc. The filtrate was basified with a 10% sodium hydroxide solution until pH=10 (2000 ml) and the mixture extracted with ethyl acetate (2000 ml). The combined organic extracts were washed with brine (1000 ml), dried and concentrated in vacuo to an oil, which was purified by flash chromatography (eluting with EA) to give the title compound as a white solid (8.24 g). M.p.115°–6° T.l.c. EA-MeOH (95:5), $R_f$ 0.25.

Intermediate 6

3-Amino-2,4-dioxo-1-(3-methyl-1-butyl)-2,3,4,5-tetrahydro-1H-1,5-benzodiazepine

Ammonium cerium (IV) nitrate (17.45 g) was added to a solution of the intermediate 5 (3.0 g) in acetonitrile (90 ml) and water (10 ml). The solution was stirred at 23° for 36 h, then concentrated in vacuo to a slurry solid. This material was diluted with a 10% sodium hydroxide solution (150 ml), stirred at 23° for 30 min, then inorganic salts were filtered off. The aqueous solution was extracted with ethyl acetate (4×100 ml). The combined organic extracts were washed with brine (300 ml), dried and concentrated in vacuo to give an oil, that was purified by flash chromatography (eluting with DCM-MeOH 95:5) to give the title compound as a white solid (0.6 g). M.p.148°–150° T.l.c. DCM-MeOH (95:5), $R_f$ 0.20.

Intermediate 7

N-[2,4-dioxo-1-(3-methyl-1-butyl)-2,3,4,5-tetrahydro-1H-1,5-benzodiazepin-3-yl]-N'-phenylurea Phenyl isocyanate (0.183 ml) was added to a solution of the intermediate 6 (0.4 g) in dry dichloromethane (5 ml) under a nitrogen atmosphere. The mixture was stirred at 23° for 30 min, then concentrated in vacuo. The residue was triturated with diethyl ether to give the title compound as a white solid (0.478 g). M.p. 249°–250°. T.l.c. DCM-MeOH (95:5), $R_f$ 0.38.

Intermediate 8

N-[2,4-dioxo-1-(3-methyl-1-butyl)-2,3,4,5-tetrahydro-1H-1,5-benzodiazepin-3-yl]-N'-(4-methoxyphenyl)urea 4-Methoxyphenyl isocyanate (0.1 ml)was added to a solution of the intermediate 6 (0.19 g) in dry dichloromethane (5 ml) under a nitrogen atmosphere. The mixture was stirred at 23° for 30 min, then concentrated in vacuo. The residue was triturated with diethyl ether to give the title compound as a white solid (0.197 g). M.p. 150°–152°. T.l.c. EA-MeOH (95:5), $R_f$ 0.78.

Intermediate 9

N-[2,4-Dioxo-5-(4-methoxyphenylmethyl)-1-(3-methyl-1-butyl) -2,3,4,5-tetrahydro-1H-1,5-benzodiazepin-3-yl]-N'-phenylurea Phenyl isocyanate (0.017 ml) was added to a solution of the intermediate 5 (0.05 g) in acetonitrile (1 ml). The mixture was stirred at 23° for 30 min, then filtered to give the title compound as a white solid (0.062 g). M.p. 206°–8°. T.l.c. CH-EA(1:1), $R_f$ 0.4.

Intermediate 10

1-(3-methyl-1-butyl) amino-2-nitrobenzene

A solution of amino 3-methylbutane (1.5 g) in THF (20 ml) was dropped into a solution of 2-fluoronitrobenzene (2.4 g) in THF (20 ml), at 23° under a nitrogen atmosphere. The mixture was stirred at 23° for 3 h, then heated at reflux for 1.5 h. The mixture was allowed to cool to 23°, then concentrated under vacuum to give a crude compound which was purified by flash chromatography on silica gel using CH-EA 9/1 as eluants to give the title compound as a yellow oil (2.12 g). T.l.c. CH-EA (8/2), $R_f$ 0.79. IR:3383 (NH); 1620 (C=C) cm$^{-1}$.

Intermediate 11

2-(3-methyl-1-butyl) amino-aniline

A solution of potassium carbonate (9.1 g) and sodium hydrosulfite (8 g) in water (50 ml) was added to a mixture of intermediate 10 (2.12 g) in ethanol (30 ml) and water (70 ml). The mixture was stirred at 23° for 1 h, then acidified with conc. hydrochloric acid until pH=3. The mixture was then basified with a 10% sodium hydroxide solution until pH=10 and extracted with ethyl acetate (2×100 ml); the combined extracts were washed with brine (150 ml), dried and concentrated in vacuo to give the title compound as a brown solid (1.8 g). T.l.c. CH-EA (8/2), Rf 0.36. IR:3420 (NH); 1620 (C=C) cm$^{-1}$.

Intermediate 12

N-(2,2-dimethylethoxycarbonyl)-N'-(3-methyl-1-butyl)-1,2-phenylenediamine

Di-t-butyl dicarbonate (2.44 g) and sodium hydrogen carbonate (1.42 g) were added to the solution of intermediate 11 (3 g ) in THF (50 ml)/water (40 ml); the mixture was stirred at 30° for 1.5 h and concentrated in vacuo. The residue was diluted with ethyl acetate (150 ml) and washed with water(50 ml) and brine (50 ml). The organic layer was dried and concentrated in vacuo to an oil, which was purified by flash chromatography (eluting with CH/EA 9/1) to give the title compound as a wax (3.1 g). T.l.c. CH-EA (9:1), Rf=0.37. IR:3420 (NH); 1722-1697 (C=O) cm$^{-1}$.

Intermediate 13

N-(2,2-dimethylethoxycarbonyl)-N'-[2-(1-benzyloxycarbonylamino-1-ethoxycarbonyl)-2-oxoethyl]-N'-(3-methyl-1-butyl)1,2-phenylenediamine To a solution of benzyloxycarbonylamino malonic acid monoethyl ester (0.90 g) in ethyl acetate (40 ml), N,N'-Dicyclohexycarbodiimide (0.76 g) and 1-Hydroxybenzotriazole hydrate (0.55 g) were added. After complete addition the mixture was stirred at 20° for 1 h, then a solution of intermediate 12 (0.88 g ) in ethyl acetate (20 ml) was added and stirring was continued for 2 h. The reaction mixture was then heated at reflux for 4 h and left at 20° for 20 h, filtered, and washed with water (50 ml) and brine (50 ml). The organic layer was dried, concentrated in vacuo and the residue was purified by flash chromatography (eluting with CH/EA 9/1) to give the title compound as an oil (0.64 g). T.l.c. CH-EA (8:2), Rf 0.33. IR:3500-3300 (NH); 1726-1672 (C=O) cm$^{-1}$.

Intermediate 14

1-(3-methyl-1-butyl)-3-benzyloxycarbonylamino-2,4-dioxo -2,3,4,5-tetrahydro-1H-1,5-benzodiazepine Concentrated hydrocloric acid (5 ml) was added to a suspension of intermediate 13 (0.64 g) in ethanol (15 ml). The mixture was stirred at 23° for 2 h, diluted with ethyl acetate, washed with water, dried and concentrated in vacuo to an oil (0.49 g ), which was purified by flash chromatography (eluting with to give the title compound as a white foam (0.23 g). T.l.c. EA-CH 1:1, Rf 0.59. IR:3431,3256 (NH); 1734,1717 (C=O) cm$^{-1}$.

Intermediate 15

5-[2-(diethylamino)ethyl]-1-(3-methyl-1-butyl)-3-benzyloxycarbonylamino -2,4-dioxo-2,3,4,5-tetrahydro-1H-1,5-benzodiazepine A solution of intermediate 14 (0.22 g) and potassium carbonate (0.24 g) in acetone (30 ml)/water (1 ml) was stirred at reflux for 6 h. The solution was concentrated in vacuo, the residue was diluted with ethyl acetate (150 ml) and washed with water (50 ml) and brine (50 ml). The organic layer was dried and concentrated in vacuo to an oil, which was purified by flash chromatography (eluting with EA-MeOH 9:1) to give the title compound as an oil (0.194 g). T.l.c. EA-CH (3:1), Rf=0.23. IR:3400 (NH); 1697-1668 (C=O) cm$^{-1}$.

Intermediate 16

3-amino-5-[2-(diethylamino)ethyl]-1-(3-methyl-1-butyl)-2,4-dioxo-2,3,4,5-tetrahydro-1H-1,5-benzodiazepine 5% Pd/C (0.04 mg) was added to a solution of intermediate 15 (0.18 g) in methanol (20 ml) and the mixture was hydrogenated at 1 atm. for 2 h. The catalyst was filtered over celite and the filtrate concentrated in vacuo and the residue was dissolved in ethyl acetate (100 ml), washed with water (100 ml), brine (10 ml), dried and concentrated in vacuo to give the title compound as a wax (0.27 g). T.l.c. EA-MeOH (1:1), Rf 0.3. IR: 1680-1651 (C=O) cm$^{-1}$.

Intermediate 17

N-(1-Adamantylcarbonyl)-N'-(4-Methoxyphenylmethyl)-1,2-phenylenediamine

1-Adamantanecarbonyl chloride (1.91 g )) was dropped into a solution of intermediate 2 (1.83 g ) and triethylamine (1.45 ml) in dry THF (100 ml at 23°, under a nitrogen atmosphere. The mixture was stirred at reflux for 3 h, allowed to cool to 20°, then diluted with ethyl acetate (120 ml) washed with brine (150 ml), dried, and concentrated in vacuo. This material (3.21 g) was crystallised from DCM/CH to give the title compound as a white solid (2.3 g). T.l.c. CH-EA (8:2), R$_f$ 0.34 IR:3393, 3304 (NH) cm$^{-1}$.

Intermediate 18

N-(1-Adamantylmethyl)-N'-(4-Methoxyphenylmethyl)-1,2-phenylenediamine.

Borane dimethylsulfide complex (10M solution; 15 ml) was added dropwise, under a nitrogen atmosphere, to a solution of intermediate 17 (2.3 g) in dry THF (70 ml) previously heated at reflux. Dimethyl sulfide and THF (50 ml) were distilled and the solution was allowed to cool to r.t., then a 10% potassium carbonate solution (30 ml) was added and the mixture was stirred at 20° for 40 min. Then it was diluted with methanol (20 ml) and stirred at reflux for 3 h, then at 20° for 20 h. ethyl acetate (100 ml) was added; the layers were separated the organic extracts washed with brine (2×50 ml), dried and concentrated in vacuo to an oil (0.20 g), which was purified by flash chromatography (eluting with CH-EA 9:1) to give the title compound (0.2 g)as a white solid. m.p 132-134. T.l.c. CH-EA (9:1), R$_f$0.63.

Intermediate 19

1-(1-Adamantylmethyl)-dioxo-5-(4-methoxyphenylmethyl)-3-phenylhydrazono-2,3,4,5-tetrahydro-1H-1,5-benzodiazepine Intermediate 18 (1.22 g) and 2-phenylhydrazonomalonyldichloride (0.940 g) were each taken up in THF (40 ml) and dropped in a flask containing THF (40 ml) under a nitrogen atmosphere. After complete addition, the solution was heated at 50° for 4 h. The solution was diluted with ethyl acetate (100 ml) and washed with saturated sodium hydrogen carbonate (2×100 ml) and brine (2×80 ml), dried and concentrated in vacuo to give the title compound as a yellow foam (1.64 g). M.p.170°-88° T.l.c. CH-EA (8:2), R$_f$ 0.60. IR:3441 (NH); 1661,1653 (C=O) cm$^{-1}$;

Intermediate 20

1-(1-Adamantylmethyl)-3-amino-2,4-dioxo-5-(4-methoxyphenylmethyl)-2,3,4,5-tetrahydro-1H-1,5-benzodiazepine Zinc dust (1.46 g) was added to a suspension of the intermediate 19 (1.36 g) in acetic acid (30 ml). The mixture was stirred at 20° for 18 h, then a further amount of Zinc dust (0.30 g) in acetic acid (3 ml) was added a stirring continued for 1 h. The mixture was decanted from zinc, the filtrate diluted with ethyl acetate (150 ml), washed with saturated sodium hydrogen carbonate (2×150 ml) and brine (200 ml), dried and concentrated in vacuo to an oil (1.31 g), which was purified by flash chromatography (eluting with EA, then EA/Methanol 95/5) to give the title compound as a pale yellow solid (0.90 g). M.p.223°-5° T.l.c. DCM-MeOH (95:5), R$_f$ 0.34. IR:1700 and 1670 (C=O) cm$^{-1}$;

Intermediate 21

1-(1-Adamantylmethyl)-3-amino-2,4-dioxo-2,3,4,5-tetrahydro-1H-1,5-benzodiazepine Ammonium cerium (IV) nitrate (3.85 g) was added to a solution of the intermediate 20 (0.80 g) in acetonitrile (125 ml) and water (5 ml). The solution was stirred at 23° for 36 h, then water (5 ml) was added to the suspension and stirring continued for 30 h at 50°. The solution was concentrated in vacuo to a slurry solid. This material was diluted with a 10% sodium hydroxide solution (250 ml) and stirred at 23° for 1 h, then inorganic salts were filtered off. The aqueous solution was extracted with ethyl acetate (2×150 ml), the combined organic extracts were washed with brine (300 ml), dried and concentrated in vacuo to give an oil (0.750 g), that was purified by flash chromatography (eluting with DCM-MeOH 95:5) to give the title compound as a white solid (0.500 g). T.l.c. DCM-MeOH (95:5), R$_f$ 0.34. IR:3213-3126 (NH and NH$_2$), 1705,1668 and 1660 (C=O) cm$^{-1}$;

Intermediate 22

N -[(1-Adamantylmethyl)-2,4-dioxo-2,3,4,5-tetrahydro -1H-1,5-benzodiazepin-3-yl]-N'-phenylurea Phenyl isocyanate (0.05 ml) was added to a solution of the intermediate 21 (0.14 g) in dry acetonitrile (10 ml) under a nitrogen atmosphere. The mixture was stirred at 23° for 30 min, then the solid was filtered off, washed with acetonitrile to give the title compound as a white solid (0.146 g). M.p.>280°. T.l.c. DCM-MeOH (95:5), R$_f$ 0.46. IR: 3383, 3215 (NH), 1697 and 1676 and 1665 (C=O); 1597 (C=C) cm$^{-1}$.

Intermediate 23

1-(1-Adamantylcarbonylamino)-2-nitrobenzene

A solution of 1-adamantanecarbonyl chloride (17.95 g) in acetone (60 ml) was dropped into a solution of 2-nitroaniline (10.4 g) and triethylamine (12.6 ml) in acetone (50 ml), at ° under a nitrogen atmosphere. The mixture was stirred at 23° for 22 h; then further acetone (50 ml) was added. The mixture was heated at 70° for 3 h. The mixture was allowed to cool to 23°, then filtered; the brown solid obtained was crystallized from acetone to give the title compound as a yellow solid (17.3 g). T.l.c. CH-EA (10:2), Rf 0.67. M.p. 111°-4°.

Intermediate 24

1-(1-Adamantylmethylamino)-2-nitrobenzene

Borane dimethylsulfide complex (10M solution; 6.0 ml) was added, dropwise, under a nitrogen atmosphere, to a solution of intermediate 23 (13.5 g) in dry toluene (160 ml) previously cooled to 10°. The solution was stirred at 10° for 15 min, then heated at 110° for 1 h. The solution was allowed to cool to room temperature, then a 10% potassium carbonate solution (50 ml) was added and the mixture was stirred at 23° for 40 min. The layers were separated; the organic extracts was washed with brine (50 ml), dried and concentrated in vacuo to a slurry solid, which was purified by flash chromatography (eluting with CH-EA 10:1) to give the title compound as an orange solid (7.0 g). T.l.c. CH-EA (10:1), Rf 0.68. M.p. 106°–109°.

Intermediate 25

2-(1-Adamantylmethylamino)-aniline

A solution of potassium carbonate (23.2 g) and sodium hydrosulfite (20.9 g) in water (150 ml) was added to a mixture of intermediate 24 (6.9 g) in ethanol (50 ml) and water (130 ml). The mixture was stirred at 23° for 30 min, then acidified with conc. hydrochloric acid until pH=3. The mixture was then basified with a 10% sodium hydroxide solution until pH=10 and concentrated to half volume. The residue was extracted with ethyl acetate (2×300 ml); the combined extracts were washed with brine (150 ml), dried and concentrated in vacuo to a residue, which was purified by flash chromatography (eluting with CH-EA 10:2) to give the title compound as a grey solid (5.0 g). T.l.c. CH-EA (10:2), Rf 0.36. M.p. 101°–104°.

Intermediate 26

N-1-Adamantylmethyl-N'-[2-(4-morpholino)ethyl]-1,2-phenylenediamine

A solution of intermediate 25 (1.3 g), sodium iodide (0.76 g) and 2-(4-morpholino)ethyl chloride hydrochloride (0.94 g) in dry dimethylformamide (40 ml) was heated at 160° for 4 h under a nitrogen atmosphere. The solution was cooled to 23° and concentrated in vacuo. The residue was diluted with ethyl acetate (150 ml) and washed with a 10% sodium hydroxide solution (50 ml) and brine (50 ml). The organic layer was dried and concentrated in vacuo to an oil, which was purified by flash chromatography (eluting with CH-EA 6:4) to give the title compound as a brown oil (0.55 g). T.l.c. CH-EA (1:1), Rf=0.39.

Intermediate 27

1-(1-Adamantylmethyl)-2,4-dioxo-5-[2-(4-morpholino)ethyl]-3-phenylhydrazono-2,3,4,5-tetrahydro-1H -1,5-benzodiazepine A solution of the intermediate 26 (0.5 g) in ethyl acetate (20 ml) was added, dropwise, to a solution of the 2-phenylhydrazonomalonyldichloride (0.4 g) in ethyl acetate (30 ml) at 23° under a nitrogen atmosphere. After complete addition the solution was heated at 80° for 1 h. The solution was cooled to 23° and washed with a 10% sodium hydroxide solution (30 ml) and brine (50 ml). The organic layer was dried, concentrated in vacuo and the residue was purified by flash chromatography (eluting with CH-EA 1:5) to give the title compound as a yellow solid (0.45 g). M.p. 110°–120°. T.l.c. CH-EA (1:5), Rf 0.48.

Intermediate 28

1-(1-Adamantylmethyl)-3-amino-2,4-dioxo-5-[2-(4-morpholino)ethyl]-2,3,4,5-tetrahydro-1H-1,5-benzodiazepine Zinc dust (0.4 g) was added to a solution of the intermediate 27 (0.45 g) in glacial acetic acid (20 ml). The mixture was stirred at 23° for 1.5 h, then decanted from zinc. The organic layer was concentrated in vacuo, then diluted with ethyl acetate (50 ml) and washed with a 10% sodium hydroxide solution (20 ml) and brine (20 ml). The organic layer was dried and concentrated in vacuo to a yellow oil, which was purified by flask chromatography (eluting with EA-MeOH 10:1) to give the title compound as a white solid (0.25 g). M.p.75°–80°. T.l.c. EA-MeOH 10:1, Rf0.11.

Intermediate 29

N-(1-Adamantylmethyl)-N'-[2-(1-pyrrolidino)ethyl]-1,2-phenylenediamine

A solution of intermediate 25 (2.0 g), sodium iodide (1.17 g) and 2-(1-pyrrolidino)ethyl chloride hydrochloride (1.33 g) in dry dimethylformamide (40 ml) was heated at 160° for 4 h under a nitrogen atmosphere. The solution was cooled to 23° and concentrated in vacuo. The residue was diluted with ethyl acetate (150 ml) and washed with a 10% sodium hydroxide solution (50 ml) and brine (50 ml). The organic layer was dried and concentrated in vacuo to an oil, which was purified by flash chromatography (eluting with EA-MeOH 95:5) to give the title compound as a brown oil (0.54 g). T.l.c. EA-MeOH (9:1), Rf=0.33.

Intermediate 30

1-(1-Adamantylmethyl)-2,4-dioxo-5-[2-(1-pyrrolidino)ethyl]-3-phenylhydrazono-2,3,4,5-tetrahydro-1H-1,5-benzodiazepine A solution of the intermediate 29 (0.5 g) in ethyl acetate (20 ml) was added, dropwise, to a solution of the 2-phenylhydrazonomalonyldichloride (0.416 g) in ethyl acetate (30 ml) at 23° under a nitrogen atmosphere. After complete addition the solution was heated at 80° for 3 h. The solution was cooled to 23° and washed with a 9M ammonium hydroxide solution (25 ml) and brine (50 ml). The organic layer was dried, concentrated in vacuo and the residue was purified by flash chromatography (eluting with EA-MeOH 10:1) to give the title compound as a yellow solid (0.27 g). M.p. 105°–110°. T.l.c. EA-MeOH (10:1), Rf 0.44.

Intermediate 31

1-(1-Adamantylmethyl)-3-amino-2,4-dioxo-5-[2-(1-pyrrolidino)ethyl]-2,3,4,5-tetrahydro-1H-1,5-benzodiazepine Zinc dust (0.23 g) was added to a solution of the intermediate 30 (0.25 g) in glacial acetic acid (20 ml). The mixture was stirred at 23° for 15 min. The mixture was decanted from zinc, diluted with further ethyl acetate (25 ml) and washed with a 10% sodium hydroxide solution (50 ml) and brine (50 ml). The organic layer was dried and concentrated in vacuo to a yellow oil, which was purified by flash chromatography (eluting in gradient from EA-MeOH 9:1 to EA-MeOH 7:3) to give the title compound as a white foam (0.15 g). T.l.c. EA-MeOH 7:3, Rf 0.3.

Intermediate 32

N-(1-Adamantylmethyl)-N'-[3'-(1,1 dimethylethyloxycarbonyl)-2',2'-dimethyl -4'-methylen-1,2-phenylene diamine To a solution of intermediate 25 (0.100 g) and 1,1-dimethylethyl (R) -4-formyl-2,2-dimethyl-3-oxazolidinecarboxylate (0.125 g) in methanol (10 ml), acetic acid (0.027 ml) and sodium cyanoborohydride (0.050 g ) were added The solution was stirred at 23° for 1 h, then saturated sodium hydrogen carbonate solution was added (50 ml) and the reaction mixture extracted with ethyl acetate (50 ml). The organic extracts were washed with brine (50 ml), dried and concentrated in vacuo to an oil, which was purified by flash chromatography (eluting with CH-EA 9/1) to give the title compound as a foam (0.100 g). T.l.c. CH-EA (5:25), Rf=0.4.

Intermediate 33

1-(1-Adamantylmethyl)-2,4-dioxo-5-[3'-(1,1-dimethyl ethyloxy carbonyl) -2',2'-dimethyl-4'-methylen-oxazolidine]-3-phenylhydrazono-2,3,4,5-tetrahydro -1H-1,5-benzodiazepine A solution of the intermediate 32 (5.8 g) in THF (20 ml) and a solution of phenylhydrazonomalonyldichloride (4.5 g) in THF (50 ml) were added, dropwise, to a suspension of Potassium carbonate in THF (20 ml) at 23° under a nitrogen atmosphere. After complete addition the solution was heated at 80° for 2 h. The solution was cooled to 23° and washed with a 10% sodium hydroxide solution (30 ml) and brine (50 ml). The organic layer was dried, concentrated in vacuo and the residue was purified by flash chromatography (eluting with CH-EA 8/2) to give the title compound as a foam (4.9 g). T.l.c. CH-EA (2:1), Rf0.8.

Intermediate 34

1-(1-Adamantylmethyl)-3-amino-2,4-dioxo-5-[3'-(1,1-dimethyl ethyloxy carbonyl) -2',2'-dimethyl-4'-methylen-oxazolidine]-2,3,4,5-tetrahydro -1H-1,5-benzodiazepine 10% Pd/C (0.33 g ) and p-toluensulfonic acid (0.325 g) were added to the solution of the intermediate 33 (1.0 g) in methanol (100 ml). The mixture was hydrogenated at 23° at 4 atm. for 1 h, then filtered on celite, and concentrated in vacuo to give the title compound as a white solid (0.25 g). T.l.c. EA-MeOH 26:4, Rf 0.4.

Intermediate 35

N-[1-(1-Adamantanemethyl)-2,4-dioxo-5-[3-hydroxy-2(R)-(dimethylethyloxycarbonyl)amino-1-propyl]-2,3,4,5-tetrahydro-1H-1,5-benzodiazepin-3-yl]-N'-phenylurea ISOMER 1 and ISOMER 2

The solution of the intermediate 34 (3.30 g) in trifluoro acetic acid/dichloromethane (50 ml; 0.5M ) was stirred at 20° for 1 h; 5% sodium hydrogen carbonate solution (100 ml) was added, the organic phase was separated, washed with brine (100 ml), dried and concentrated under vacuum to give a residue which was taken up in acetonitrile (50 ml). To the resulting solution, phenyl isocyanate (0.072 ml) was added; the reaction mixture was stirred at 23° for 15 h, concentrated under vacuum to give the title compound as a mixture of isomers 1 and 2. This mixture was separated by purified by flash chromatography on silica using CH/EA 9/1 as eluant to give the title compound (ISOMER 1 ) as a white solid (0.6 g). M.p. 188°. T.l.c. CH-EA 1:1, Rf0.6. Rf0.6. IR:3431 (NH, OH), 1699 (C=O) cm–1; 1H-NMR: 7.66 (m); 7.46-7.24 (m); 7.05 (m); 6.99 (s); 6.34 (d); 5.42 (d);5.16 (d); 4.39 (d); 4.30-4.18 (m); 3.96-3.80 (m); 3.66 (t); 3.49 (dd); 3.19 (d); 1.83 (m); 1.66-1.10 (m); 1.44 (s). Continuing the elution, some mixed fractions were obtained (0.34 g) and then the title compound (ISOMER 2 ) was eluted (0.9 g ) T.l.c. CH-EA 1:1, Rf0.6. IR: 3364 (NH, OH), 1697 (C=O) cm–1; 1H-NMR: 7.70-7.10 (m); 6.92 (m);6.69(d); 5.37 (bd;); 5.16 (d); 4.38 (d); 4.24-4.0 (m); 3.96-3.68 (m); 3.70-3.44 (m); 3.35 (d); 1.85 (m); 1.68-1.20 (m);1.41 (s).

Intermediate 36

N-Cyclohexylmethyl-1,2-phenylenediamine

A solution of 1,2-phenylenediamine (5.0 g), cyclohexylomethyl bromide (7.0 g) and sodium iodide (7.0 g) in dry dimethylformamide (250 ml) was stirred at 32° for 24 h under a nitrogen atmosphere. The solution was diluted with water (200 ml) and extracted with ethyl acetate (4×200 ml); the combined organic extracts were washed with brine (500 ml), dried and concentrated in vacuo to an oil, which was purified by flash chromatography (eluting with CH-EA 8:2) to give the title compound as a white solid (1.8 g). T.l.c. HC-EA (1:1), Rf=0.55. IR:3400, 3371 and 3271 (NH2 and NH) cm–1.

Intermediate 37

N-Cyclohexylmethyl-N'-[2-(diethylamino)ethyl)]-1,2-phenylenediamine a solution of Intermediate 36 (2.42 g), sodium iodide (1.22 g) and 2-diethylaminoethyl chloride hydrochloride (2.0 g) in dry dimethylformamide (100 ml) was heated at 160° for 4 h under a nitrogen atmosphere. The solution was cooled to 23° and concentrated in vacuo. The residue was diluted with a 10% sodium hydroxide solution (100 ml) and extracted with ethyl acetate (200 ml). The organic layer was washed with brine (150 ml), dried and concentrated in vacuo to an oil, which was purified by flash chromatography (eluting with CH-EA 4:6) to give the title compound as a brown oil (1.7 g). T.l.c. CHEA (1:1), Rf=0.26. IR:1601 (C=C)cm–1.

Intermediate 38

1-Cyclohexylmethyl-2,4-dioxo-5-[2-(diethylamino) ethyl]-3-phenylhydrazono-2,3,4,5-tetrahydro-1H-1,5-benzodiazepine A solution of the Intermediate 37 (1.7 g) in ethyl acetate (50 ml) was added, dropwise, to a solution of the 2-phenylhydrazonomalonyldichloride (1.37 g) in ethyl acetate (50 ml) at 23° under a nitrogen atmosphere. After complete addition the solution was heated at 80° for 4 h. The solution was cooled to 23° and washed with a 10% sodium hydroxide solution (50 ml) and brine (50 ml). The organic layer was dried, concentrated in vacuo and the residue was purified by flash chromatography (eluting with CH-EA 6:4) to give the title compound as a yellow foam (1.0 g). T.l.c. CH-EA (1:1), Rf 0.34. IR:3441-3186 (NH); 1661 (C=O) cm–1.

Intermediate 39

3-Amino-1-cyclohexylmethyl-5-[2-(dimethylamino) ethyl]-2,4-dioxo -2,3,4,5-tetrahydro-1H-1,5-benzodiazepine Zinc dust (0.3 g) was added to a solution of the intermediate 38 (0.38 g) n glacial acetic acid (5 ml). The mixture was stirred at 23° for 3 h, then decanted from zinc. The filtrate was basified with a 10% sodium hydroxide solution until pH=10 and extracted with ethyl acetate (2×40 ml). The combined organic extracts were washed with brine (60 ml), dried and concentrated in vacuo to an oil, which was purified by flash chromatography (eluting with DCM-MeOH 9:1) to give the title compound as a yellow solid (0.17 g). M.p.94°-5°. T.l.c. DCM-MeOH 85:15, Rf0.78. IR:1695 and 1664 (C=O) cm–1.

Intermediate 40

5-Fluoro-N-[2-(4-morpholino)ethyl]-2-nitroaniline

A solution of 2-(N-morpholino)ethylamine (2.45 g) in tetrahydrofuran (10 ml) was added dropwise to a solution of 2,4-difluoronitrobenzene (3.0 g) in tetrahydrofuran (30 ml) and the mixture was stirred at 23° for 1.5 h. The mixture was concentrated in vacuo, crystallized from DCM-Petrol and purified by flash chromatography (eluting with CH-EA 1:1) to give the title compound as a yellow solid (3.0 g). T.l.c. CH-EA (1:1) $R_f$=0.39. M.p. 103°-4°. IR (nujol): 3400 (N-H); 1632 (C=C); 1570, 1312 (NO2) cm–1.

Intermediate 41

5-Fluoro-N'-[2-(4-morpholino)ethyl]-1,2-benzenediamine

Potassium carbonate (9.7 g) and sodium hydrosulfite (8.4 g) were added to a suspension of intermediate 40 in ethanol-water 1:1 (150 ml) and the mixture was stirred at 23° for 1 h. The mixture was concentrated in vacuo, acidified to pH=3 with conc. hydrochloric acid and extracted with ethyl acetate (150 ml). The aqueous layer was basified with a 10% sodium hydroxide solution then extracted with ethyl acetate(2×150 ml). The organic layer was washed with brine (200 ml), dried and concentrated in vacuo to give the title compound as a brown oil (1.9 g). T.l.c. EA-MeOH (9:1) $R_f$=0.28. IR (nujol) 3337 (NH); 1614 (C=C) cm–1.

Intermediate 42a

N-(1-Adamantylcarbonyl)-4-fluoro-N'-[2-(4-morpholino) ethyl]-1,2-benzenediamine

A solution of 1-adamantanecarbonyl chloride (1.78 g) in dry THF (30 ml) was added dropwise to a mixture of intermediate 41 (1.9 g) and triethylamine (1.36 ml) in dry THF (70 ml). The mixture was heated at 60° for 1.5 h, then the solvents were evaporated in vacuo. The residue was taken up with ethyl acetate (200 ml), washed with water (100 ml) and brine (50 ml), dried and concentrated in vacuo to give the title compound as a white solid (3.23 g). T.l.c. CH-EA (1:1) $R_f$=0.31. M.p. 172°-4°. IR (nujol) 3375, 3314 (NH); 1647 (C=O); 1618, 1600 (C=C) cm–1.

Intermediate 42b
N-(1-Adamantylmethyl)-4-fluoro-N'-[2-(4-morpholino)ethyl]-1,2-benzenediamine A solution of Vitride [sodium dihydro-bis(2-methoxyethoxy)aluminate](5.7 ml) in toluene (10 ml) was added dropwise over 15 min to a cooled (0° C.) suspension of intermediate 42a (3.23 g) in toluene (40 ml). The mixture was stirred at 0° for further 10 min, then at 23° for 30 min. The reaction was quenched by adding ethyl acetate (20 ml) at 0°, over 15 min. After additional 15 min, the mixture was diluted with more ethyl acetate (100 ml) and washed with water (3×100 ml); the aqueous layer was extracted with ethyl acetate (200 ml), the combined organic extracts were washed with brine (150 ml), dried and concentrated in vacuo. The residue was purified by flash chromatography (eluting with CH-EA 7:3) to give the title compound as a wax (2.2 g). T.l.c. CH-EA (1:1) $R_f$ 0.49. IR (nujol) 3300 (NH); 1612 (C=C) $cm^{-1}$.

Intermediate 43
1-Adamantylmethyl-2,4-dioxo-7-fluoro-5-[2-(4-morpholino)ethyl]-3-phenylhydrazono-2,3,4,5-tetrahydro-1H-1,5-benzodiazepine A solution of phenylhydrazonomalonyl dichloride (1.43 g) in ethyl acetate (50 ml) was added dropwise to a solution of intermediate 42b (2.05 g) in ethyl acetate (30 ml) and the mixture was heated at 60° for 3 h. The mixture was diluted with ethyl acetate (150 ml) and washed with a 5% sodium hydroxide solution (100 ml); the aqueous layer was reextracted with ethyl acetate (100 ml) and the combined organic layers were washed with brine (100 ml), dried and concentrated in vacuo. The residue was purified by flash chromatography (eluting with CH-EA 7:3) to give the title compound as a yellow foam (2.05 g). T.l.c. CH-EA (1:1) $R_f$=0.42. IR (nujol) 1663 (C=O); 1603, 1590 (C=C) $cm^{-1}$.

Intermediate 44
1-Adamantylmethyl-3-amino-2,4-dioxo-7-fluoro-5-[2-(4-morpholino)ethyl]-2,3,4,5-tetrahydro-1H-1,5-benzodiazepine Zinc dust (1.76 g) was added to a solution of intermediate 43 (2.05 g) in glacial acetic acid (30 ml) and the mixture was stirred at 23° for 4 h; then, it was filtered over celite, washing the solid with ethyl acetate, and the filtrate was basified with a 10% sodium hydroxide solution. The layers were separated and the aqueous phase was extracted with ethyl acetate (2×50 ml); the combined organic extracts were washed with brine (50 ml), dried and concentrated in vacuo. The residue was purified by flash chromatography (eluting with EA-MeOH 9:1) to give the title compound as a white foam (1.1 g). T.l.c. EA-MeOH (8:2) $R_f$ 0.5. IR (nujol): 3400 (NH), 1693-1663 (CO); 1605 (C=C) $cm^{-1}$.

Intermediate 45
N-(3-methyl-1-butyl)-N'-[(2-(4-morpholino)ethyl]-1,2-benzenediamine Glacial acetic acid (1.5 ml) was added to a solution of 2-[-2-(4-morpholinoethyl) amino]aniline (5.7 g) and 3-methylbutyraldehyde (2.7 ml) in methanol (100 ml). The mixture was stirred at 23° for 10 min., then, sodium cyanoborohydride (3.5 g) was added portionwise. Stirring was continued for 3 h, then the mixture was concentrated in vacuo; the residue was diluted with ethyl acetate (500 ml), washed with a 5% sodium bicarbonate solution (2×100ml) and brine (150 ml), dried and the solvents were evaporated in vacuo. Purification of the crude material by flash chromatography (eluting with CH-EA 55:45) afforded the title compound as a colorless oil (3.3 g). T.l.c. CH-EA (1:1), $R_f$ 0.33. IR: 1601 (C=O) $cm^{-1}$; $^1$H-NMR: 6.79; 6.66 (m); 3.71; 3.13 (m); 2.69; 2.49; 1.79; 1.58; 0.97.

Intermediate 46
2,4-Dioxo-1-(3-methyl-1-butyl)-5-[(2-(4-morpholino)ethyl]-3-phenylhydrazono-2,3,4,5-tetrahydro-1H-1,5-benzodiazepine A solution of 2-phenylhydrazonomalonyl dichloride (3.6 g) in ethyl acetate (250 ml) was added dropwise to a solution of intermediate 45 (3.3 g) in ethyl acetate (150 ml) and the mixture was stirred under reflux for 2 h. The mixture was concentrated in vacuo and the residue was purified by flash chromatography (eluting with EA), to give the title compound as a yellow solid (3.6 g). T.l.c. CH-EA (1:1), $R_f$ 0.13. M.p. 76°-8°. IR: 1653 and 1626 (C=O) $cm^{-1}$;

Intermediate 47
3-Amino-2,4-dioxo-1-(3-methyl-1-butyl)-5-[2-(-4-morpholino)ethyl]-2,3,4,5-tetrahydro-1H-1,5-benzodiazepine Zinc metal (3.8 g) was added portionwise to a solution of intermediate 46 (3.6 g) in glacial acetic acid (60 ml); the mixture was stirred at 23° for 15 min., then it was diluted with ethyl acetate (150 ml) and filtered, washing the solid with ethyl acetate (100 ml) and a 10% sodium hydroxide solution (20 ml). More 10% sodium hydroxide solution (150 ml) was added to the filtrate, until pH=10, then the solution was extracted with ethyl acetate (150 ml). The organic layer was washed with brine (100 ml), dried and concentrated in vacuo. The residue was purified by flash chromatography (eluting with EA-MeOH 10:1) to give the title compound as a light yellow solid (1.5 g). T.l.c. EA-MeOH (10:1), $R_f$ 0.37. M.p. 117°-9° C. IR: 1691 (C=O) $cm^{-1}$;

Intermediate 48
N-[2-(Hexamethyleneimino)ethyl]-N'-phenyl-1,2-benzenediamine N-Phenyl-1,2-benzenediamine (2.0 g) and 2-(hexamethyleneimino)-ethylchloride hydrochloride (2.57 g) were added to a mixture of potassium carbonate (4.48 g) and potassium iodide (2.16 g) in dry xylene and the mixture was refluxed under a nitrogen atmosphere for 2 h. The mixture was diluted with methylene chloride (100 ml), washed with a 5% ammonia solution (50 ml), water (50 ml) and brine (70 ml), dried and the solvents were evaporated in vacuo. Purification of the crude material by flash chromatography (eluting with CH-EA 6:4) to give the title compound (2.09 g) as a dark oil. T.l.c. CH-EA (4:6), $R_f$ 0.45. IR: 3252 (NH); 1597 (C=C) $cm^{-1}$;

Intermediate 49
2,4-Dioxo-1-[2-(hexamethyleneimino)ethyl]-5-phenyl -3-phenylhydrazono-2,3,4,5-tetrahydro-1H-1,5-benzodiazepine A solution of 2-phenylhydrazonomalonyl dichloride (1.81 g) in ethyl acetate (115 ml) was added dropwise to a solution of intermediate 48 (2.08 g) in ethyl acetate (115 ml) and the mixture was stirred at 23° for 1 h, then at 50° for 1 h. The mixture was washed with a 10% sodium hydroxide solution (100 ml) and brine (100 ml), dried and concentrated in vacuo. The residue was purified by flash chromatography (eluting with EA), to give the title compound as a yellow foam (2.03 g). T.l.c. EA, $R_f$ 0.34. IR: 1664 (C=O); 1591 (C=C) $cm^{-1}$;

Intermediate 50
3-Amino-2,4-dioxo-1-[2-(hexamethyleneimino)ethyl]-5-phenyl -2,3,4,5-tetrahydro-1H-1,5-benzodiazepine Ammonium formate (0.656 g) and 10% Palladium on charcoal (0.463 g) were added to a solution of intermediate 49 (0.50 g) in dry methanol (20 ml). The mixture was refluxed for 30 min under a nitrogen atmosphere, then cooled to 23° C. and filtered over celite. The filtrate was concentrated in vacuo; the residue was taken up in diethyl ether (50 ml) and extracted with a 10% hydrochloric acid solution (50 ml). The aqueous layer was neutralized with solid sodium bicarbonate, then extracted with ethyl acetate (2×50 ml). The organic layer was washed with brine (50 ml), dried and concentrated in vacuo to give the title compound as an orange foam (0.36 g). T.l.c DCM-MeOH 95:5, $R_f$ 0.42.

Intermediate 51

(S)-(+)-2-(4-toluenesulphonyloxy)-phenylacetic acid methyl ester

Method A) (S)-(+)-methyl mandelate (3.0 g) and triethylamine (6.13 ml) were dissolved in dry dichloromethane (40 ml). The mixture was cooled to 0° then 4-toluenesulphonyl chloride (6.87 g) was added under stirring. The solution was kept at this temperature for 40 min. and then was allowed to warm to 23° during 20 min. After this time, the mixture was diluted with dichloromethane (20 ml), washed with brine (50 ml), dried and concentrated in vacuo. The crude material was purified by flash chromatography (eluting with CH/EA 5:1 then 2:1) to give the title compound as a white wax (5.75 g). T.l.c. (CH/EA 2:1) $R_f$=0.54, HPLC: (+)/(−)=91.4/8.6 e.e.=82.8%, M.p.=57–58.

Method B) (S)-(+)-methyl mandelate (3.0 g) and pyridine (2.9 ml) were dissolved in dry dichloromethane (40 ml). The mixture was cooled to 0° then 4-toluenesulphonyl chloride (6.87 g) was added under stirring. The solution was kept at this temperature for 15 min. and then was allowed to warm to 23°. After 4 h the mixture was diluted with dichloromethane (50 ml), washed with HCl 5% (80 ml) and brine (80 ml), dried and concentrated in vacuo. The crude material was purified by flash chromatography (eluting with CH/EA 4:1 then 2:1) to give a colorless oil which was further purified by flash chromatography (eluting with CH/EA 5:1) to give the title compound as a white wax (2.2 g). T.l.c. (CH/EA 2:1) $R_f$=0.54, HPLC: (+)/(−)=99.8/0.2 e.e.=99.6%, M.p.=57°–58°.

Intermediate 52

[1-(1-Adamantylmethyl)-2,4-dioxo-5-[2-(4-morpholino) ethyl]-2,3,4,5-tetrahydro-1H-1,5-benzodiazepin-3-yl]-amino phenylacetic acid methyl ester (isomer 1 and isomer 2)

Diisopropylethylamine (0.348 ml) was added to a mixture of intermediate 28 (0.905 g) and intermediate 51 (1.28 g) in dry tetrahydrofuran (30 ml). The mixture was refluxed for 8 h, then it was diluted with dichloromethane (100 ml), washed with a saturated ammonium chloride solution (100 ml) and brine (100 ml), then dried and concentrated in vacuo. The crude material was purified twice by flash chromatography (eluting with CH-EA in gradient from 1:3 to 1:9, then with EA-MeOH 4:1), to give:

title compound (isomer 1)(0.336 g) as white foam as white foam. T.l.c. (EA-MeOH 24:1) $R_f$=0.65, IR: 1742, 1700, 1666 (C=O).

title compound (isomer2)(0.081 g). as a white foam. T.l.c. (EA-MeOH 24:1) $R_f$=0.61, HPLC: d.e.=90.6%, Intermediate 53

N-(tert-butoxycarbonyl)-D-phenylalanine

Di-tert-butyldicarbonate (4.32 g) was added to a solution of D-phenylalanine (3 g) in a mixture of dioxan/water (2:1, 54 ml) and sodium hydroxide 1N (18 ml). The mixture was stirred at 23° for 3 h, dioxan was evaporated in vacuo and the chilled water phase was extracted with ethyl acetate (30 ml). The water solution was acidified at pH=3 by the addition of solid citric acid and extracted with ethyl acetate (2×30 ml). The organic layer was washed with brine (30 ml), dried and evaporated to give the crude title compound as an oil (4.3 g). $^1$H-NMR (CDCl3):7.4–7.1 (m),5.0–4.5(bm), 3.3–2.7(bm), 1.4(s)

Intermediate 54

N-{1-Adamantylmethyl-5-[2-(4-morpholino)ethyl]-2,4-dioxo -2,3,4,5,tetrahydro-1,5-benzodiazepin-3yl}-2-D-(3-tertbutoxycarbonyl)-3-phenylpropionamide N,N' dicyclohexylcarbodiimide (0.784 g) and 1-hydroxybenzotriazole (0.565 g) were added to a solution of intermediate 53 in ethyl acetate (150 ml). The solution was stirred at 23° for 2 h, then a solution of Intermediate 28 (1.5 g) in ethyl acetate (10 ml) was added. The resulting solution was stirred for 3 h at 23°, then filtered and concentrated in vacuo. The residue was purified by flash chromatography using a gradient of EA-CH (1:1 to pure EA) as eluant to afford the title compound (1,84 g).as a foam T.l.c. EA-CH (2:1) Rf=0.2. IR: 3400 (N-H) cm−1707, 1672 (C=O) cm$^{-1}$.

Intermediate 55

N-{1-Adamantylmethyl-5-[2-(4-morpholino)ethyl]-2,4-dioxo-2,3,4,5,tetrahydro-1H-1,5-benzodiazepine-3-yl}-2-D-amino-3-phenylpropionamide (isomer 1 and isomer 2)

Intermediate 54 (1.84 g) was dissolved in a mixture of trifluoroacetic acid (6 ml) and dichloromethane (6 ml) and stirred at 23° for 30 min. The reaction mixture was concentrated in vacuo and triturated with diethyl ether to give the trifluoroacetic salt of the title compound, which was filtered and dried (1.78 g). This salt was suspended in ethyl acetate (50 ml) and extracted with a 5% ammonia solution (70 ml). The organic layer was washed with brine, dried and concentrated in vacuo to give a white foam (1.24 g). Separation of the two diastereomers was achieved by flash chromatography eluting with a gradient of EA-MeOH (98:2 to 95:5) to give:

title compound (isomer 1) (0.618 g)as a white foam T.l.c. EA-MeOH (9.25: 0.75) Rf=0.38 title compound (isomer 2)(0.440 g) as a white foam. T.l.c. EA-MeOH (9.25:0.75) Rf=0.22. I.R:1705,1666 (C=O) cm−1.

Intermediate 56

N-{1-Adamantylmethyl-5-[2-(4-morpholino)ethyl]-2,4-dioxo -2,3,4,5-tetrahydro-1H-1,5-benzodiazepin-3-yl]-3-phenyl-2-D-(3-phenylthioureido)-propionamide Phenylisothiocyanate (0,149 g) was added to a solution of intermediate 55 (isomer 1) (0,61 g) in dichloromethane (50 ml). The solution was stirred at 23° for 3 h and at 50° for 30 min. The solvent was evaporated and the residue was purified by flash chromatography using EA-CH (1:1) as eluant to afford the title compound as a foam (0,66 g) T.l.c. EA-CH (1:1) Rf=0.38. IR 1705,1666 (C=O) cm−1.

Intermediate 57

(−)3-Amino-1-(1-adamantylmethyl)-2,4-dioxo-5-[2-(4-morpholino)ethyl]-2,3,4,5-tetrahydro-1H-1,5-benzodiazepine Method A 20% Palladium (II) hydroxide on charcoal (0.218 g) was added to a solution of intermediate 52 (isomer 1) (0.187 g) in methanol (10 ml). The mixture was hydrogenated at atmospheric pressure for 5 h, then filtered on a celite pad. After evaporation of the solvents, the crude material was purified by flash chromatography (eluting with CH-EA 1:1 then with EA-MeOH 3:2) to give the title compound as a white solid (0.140 g). T.l.c. (EA-MeOH 1:1) $R_f$=0.44. M.p. 180°–5° C. αD=−36°. −IR 3480-3350 (N-H), 1695, 1664 (C=O) cm−1.

Method B

Intermediate 57(0.65 g) was dissolved in trifluoroacetic acid (15 ml) and stirred at 60° for 30 min. The solution was concentrated in vacuo, the residue was diluted with ethyl acetate (60 ml) and washed with a 5% sodium bicarbonate solution (20 ml) and brine. The organic phase was dried and concentrated in vacuo; the residue was purified by flash chomatography using EA-CH (1:1) then EA-MeOH (9:1) as eluants to afford the title compound (0.05 g) and recovered starting material (0.508 g).

product, obtained by reaction of title compound with phenylisocyanate, had the same retention time (5.2 min) as isomer 1 of Example 11.(column: Pirkle D-DNBPG C5,(25× 2.4) eluent DCM-IPA 93:7.)

The recovered starting material (0.169 g) was reprocessed by stirring in trifluoroacetic acid (10 ml) at 40° for 22 h. After usual work-up, further title compound (0.050 g) was obtained (enantiomeric purity 97:3).

EXAMPLE 1

N-[2,4-Dioxo-1-(3-methyl-1-butyl)-5-[2-(4-morpholinyl)ethyl]-2,3,4,5-tetrahydro-1H-1,5-benzodiazepin-3-yl]-N'-phenylurea Method A Sodium hydride (19.8 mg)was added to a solution of the intermediate 7 (110 mg) in dry DMF (5 ml) under a nitrogen atmosphere. The mixture was stirred at 23° for 30 min, then 4-(2-chloroethyl)morpholine hydrochloride (67.6 mg) was added. The mixture was heated at 70° for 5 h. The mixture was cooled to 23°, then diluted with a 5% sodium hydrogen carbonate solution (30 ml) and extracted with ethyl acetate (3×30 ml). The combined organic extracts were washed with brine (60 ml), dried and concentrated in vacuo to an oil. The latter was purified by flash chromatography (eluting with EA) and the solid obtained was further purified by trituration with diethyl ether to give the title compound as a white solid (78 mg). M.p. 129°–130°. T.l.c. EA-MeOH (95:5), $R_f$ 0.46.

Method B

A mixture of the intermediate 7 (50 mg), potassium carbonate (54 mg), 4-(2-chloroethyl)morpholine hydrochloride (26.6 mg), acetone (10 ml) and water (1 ml) was stirred at 75° for 17 h. The suspension was cooled to 23°; inorganic compounds were filtered off and the filtrate was concentrated in vacuo. The residue was triturated with acetonitrile to give the title compound as a white solid (45 mg). M.p. 129°–130°. T.l.c. EA-MeOH (95:5), $R_f$ 0.46. IR:3400 (NH), 1695 and 1637 (C=O), 1601 and 1558 (C=C) cm$^{-1}$; $^1$H-NMR :7.6-7.54 (m); 7.46-7.24 (m); 7.05 (t); 6.75 (s); 6.22 (d); 5.09 (d); 4.4-4.2 (m); 3.8-3.6 (m); 2.6-2.35 (m); 1.6-1.35 (m); 0.88 (d); 0.86 (d).

EXAMPLE 2

N-[2,4-Dioxo-1-(3-methyl-1-butyl)-5-[2-(1-piperidino)ethyl]-2,3,4,5-tetrahydro-1H-1,5-benzodiazepin-3-yl]-N'-phenylurea A mixture of the intermediate 7 (50 mg), potassium carbonate (54 mg), 4-(2-chloroethyl)piperidine hydrochloride (26.33 mg), acetone (10 ml) and water (1 ml) was stirred at 75° for 18 h. The suspension was cooled to 23°; inorganic compounds were filtered off and the filtrate was concentrated in vacuo. The residue was triturated with diethyl ether to give the title compound as a white solid (44 mg). M.p. 107°–9°. T.l.c. EA-MeOH (95:5), $R_f$ 0.2. IR:3429 and 3192 (NH), 1699 and 1647 (C=O), 1601 (C=C) cm$^{-1}$; $^1$H-NMR :7.6 (m); 7.44-7.30 (m); 7.05 (t); 6.75 (s); 6.22 (d); 5.08 (d); 4.4-4.2 (m); 3.8-3.65 (m); 2.5-2.3 (m); 1.56-1.3 (m); 0.87 (d); 0.84 (d).

EXAMPLE 3

N-[5-[2-(Dimethylamino)ethyl]-2,4-dioxo-1-(3-methyl-1-butyl) -2,3,4,5-tetrahydro-1H-1,5-benzodiazepin-3-yl]-N'-phenylurea A mixture of the intermediate 7 (50 mg), potassium carbonate (54 mg), 2-dimethylaminoethylchloride hydrochloride (20.6 mg), acetone (10 ml) and water (1 ml) was heated at 75° for 20 h. The suspension was cooled to 23°; inorganic compounds were filtered off and the filtrate was concentrated in vacuo. The residue was purified by flash chromatography (eluting with EA-MeOH 95:5) to give the title compound as a white solid (45 mg). M.p. 159°–161°. T.l.c. EA-MeOH (95:5), $R_f$ 0.39. IR: 3350 (NH), 1695 and 1641 (C=O), 1601 (C=C) cm$^{-1}$; $^1$H-NMR :7.54-7.2 (m); 7.055 (t); 6.71 (s); 6.20 (d); 5.08 (d); 4.4-4.25 (m); 3.8-3.6 (m); 2.5-2.3 (m); 2.17 (s); 1.5 (m); 1.45-1.35 (m); 0.87 (d); 0.85 (d).

EXAMPLE 4

N-[2,4-Dioxo-1-(3-methyl-1-butyl)-5-[2-(4-morpholino) ethyl]-2,3,4,5-tetrahydro-1H-1,5-benzodiazepin-3-yl]-N'-(4-methoxyphenyl)urea A mixture of the intermediate 8 (0.175 g), potassium carbonate (0.178 g), 4-(2-chloroethyl)morpholine hydrochloride (0.087 g), acetone (20 ml) and water (2 ml) was stirred at 75° for 18 h. The suspension was cooled to 23°; inorganic compounds were filtered off and the filtrate was concentrated in vacuo. The residue was purified by flash chromatography (eluting with EA-MeOH 98:2) to give the title compound as a white solid (178 mg). M.p. 161°–3°. T.l.c. EA-MeOH (9:1), $R_f$ 0.53. IR: 3346 (NH), 1728, 1700 and 1653 (C=O) cm$^{-1}$; $^1$H-NMR :7.54 (m); 7.42-7.32 (m); 7.26 (d); 6.86 (d); 6.43 (s); 6.06 (d); 5.06 (d); 4.4-4.1 (m); 3.78 (s); 3.8-3.6 (m); 3.62 (t); 2.6-2.2 (m); 1.6-1.3 (m); 0.87 (d); 0.84 (d).

EXAMPLE 5

N-[2,4-Dioxo-1-(3-methyl-1-butyl)-5-[2-(4-morpholinyl)ethyl]-2,3,4,5-tetrahydro-1H-1,5-benzodiazepin-3-yl]-N'-(4-hydroxyphenyl)urea Aluminium iodide (0.194 g) was added to a solution of Example 4 (0.05 g) in dry acetonitrile (20 ml) under a nitrogen atmosphere. The solution was heated at 90° for 24 h. Further aluminium iodide (0.194 g) was added and the mixture heated at 90° for further 24 h. The mixture was cooled to 23°, diluted with water (5 ml) and a 5% sodium thiosulfate solution (25 ml) and extracted with ethyl acetate (2×30 ml). The combined organic extracts were washed with brine (50 ml), dried and concentrated in vacuo to a residue that was triturated with diethyl ether to give the title compound as a white solid (0.030 g). M.p. 104°–5° (dec). T.l.c. EA-MeOH (95:5), $R_f$ 0.2. IR: 3450 and 3340 (NH and OH), 1697 and 1663 (C=O) cm$^{-1}$; $^1$H-NMR :7.55 (m); 7.46-7.32 (m); 7.07 (m); 6.62 (m); 6.46-6.10 (m); 5.07 (d); 4.34 (m); 4.20 (m); 3.9-3.6 (m); 2.7-2.3 (m); 1.8-1.3 (m); 0.86 (d); 0.84 (d).

EXAMPLE 6

N-[5-[2-(diethylamino)ethyl]-2,4-dioxo-1-(3-methyl-1-butyl)-]-2,3,4,5-tetrahydro-1H-benzodiazepin-3-yl]-N'-phenylurea Phenyl isocyanate (0.022 ml) was added to a solution of the intermediate 16 (0.07 g) in acetonitrile (3.5 ml). The reaction mixture was stirred at 23C for 20 min, then the solid was filtered, washed with acetonitrile to give the title compound as a white solid (0.066 g). M.p 147°.

T.l.c. EA/MeOH 8:2, Rf0.64 IR: 3315 (NH), 1703 and 1666 (C=O) cm–1; 1H-NMR: 7.57 (m); 7.39 (m); 7.37-7.29 (m); 7.04 (t); 6.84 (bs); 6.26 (d); 5.08 (d); 4.36-4.2 (m);

3.74 (m); 3.62 (m); 2.63 (m); 2.49 (q); 1.48 (m);1.38 (m); 0.94 (t); 0.86 (d); 0.83 (d).

EXAMPLE 7

N-[1-(1-Adamantylmethyl)-5-[2-(dimethylamino) ethyl]-2,4-dioxo -2,3,4,5-tetrahydro-1H-1,5-benzodiazepin-3-yl]-N'-phenylurea A mixture of the intermediate 22 (0.134 g) and 80% oil suspension sodium hydride (0.020 g) in dry DMF (5 ml), was stirred at 20° for 15 min., then 2-dimethylaminoethylchloride hydrochloride (0.052 g) was added and the resulting mixture was heated at 80° for 4 h. The suspension was cooled to 23°; diluted with ethyl acetate (50 ml) and saturated sodium hydrogen carbonate solution (50 ml); the collected organic phases were washed with brine, dried and concentrated in vacuo. The residue (0.16 g) was purified by flash chromatography (eluting with EA-MeOH 9:1) to give the title compound as a white solid (0.13 g). M.p. 150-21°. T.l.c. EA-MeOH (9:1), R$_f$0.31. IR: 3400 (NH), 1697 and 1666 (C=O), cm$^{-1}$; $^1$H-NMR :7.66-7.41 (m); 7.40-7.20(m); 7.07 (m); 6.50 (bs); 6.08 (d); 5.10 (d); 4.39 (d); 4.11-3.79 (m); 3.23 (d); 2.9-2.66 (m); 2.33 (s); 1.83 (m); 1.66-1.40 (m); 1.24 (m).

EXAMPLE 8

N-[1-(1-Adamantylmethyl)-5-[3-(dimethylamino) propyl]-2,4-dioxo -2,3,4,5-tetrahydro-1H-1,5-benzodiazepin-3-yl]-N'-phenylurea A mixture of the intermediate 22 (0.103 g) and 80% oil suspension sodium hydride (0.017 g),in dry DMF (5 ml) was stirred at 20° for 15 min., then 3(-dimethylamino) propylchloride hydrochloride (0.043 g) was added and the resulting mixture was heated at 80° for 4 h. The suspension was cooled to 23°; diluted with ethyl acetate (50 ml) and saturated sodium hydrogen carbonate solution (50 ml); the collected organic phases were washed with brine, dried and concentrated in vacuo. The residue (0.12 g) was purified by flash chromatography (eluting with EA-MeOH 9:1) to give the title compound as a white solid (0.09 g). M.p. 138°-40°. T.l.c. DCM-MeOH (9:1), R$_f$0.24. IR:3315 (NH), 1699 and 1639 (C=O), 1610 (C=C) cm$^{-1}$; $^1$H-NMR :7.52-7.24 (m);; 7.04 (t); 6.87 (bs); 6.27 (d); 5.09 (d); 4.39 (d); 4.08-3.80 (m); 3.24 (d); 2.45 (m); 2.28 (s); 2.2-2.0(m); 1.98-1.70 (m); 1.6-1.2 (m).

EXAMPLE 9

N-[1-(1-Adamantylmethyl)-2,4-dioxo-5-[2-(4-morpholino)ethyl]-2,3,4,5-tetrahydro-1H-benzodiazepin-3-yl]-N'-phenylurea Phenyl isocyanate (0.041 ml) was added to a solution of the intermediate 28 (0.16 g) in acetonitrile (7 ml). The reaction mixture was stirred at 23° for 30 min, then concentrated in vacuo. The residue was triturated with diethyl ether to give the title compound as a white solid (0.1 g). M.p.188°–190°. T.l.c. CH-EA 1:1, Rf 0.18. IR: 3317 (NH), 1699 and 1666 (C=O) cm–1; 1H-NMR: 7.80 (m); 7.5-7.2 (m); 7.05 (t); 6.81 (s); 6.24 (d); 5.12 (d); 4.39 (d); 4.14 (m); 3.9-3.6 (m); 3.23 (d); 2.94-2.76 (m); 1.83 (s); 1.7-1.1 (m).

EXAMPLE 10

N-[1-(1-Adamantylmethyl)-2,4-dioxo-5-[2-(1-pyrrolidino)ethyl]-2,3,4,5-tetrahydro-1H-benzodiazepin-3-yl]-N'-phenylurea Phenyl isocyanate (0.026 ml) was added to a solution of the intermediate 31 (0.1 g) in dichloromethane (7 ml). The reaction mixture was stirred at 23° for 30 min, then concentrated in vacuo. The residue was triturated with diethyl ether to give the title compound as a white solid (0.08 g). M.p.155°–160°. T.l.c. EA-MeOH 10:1, Rf 0.43. IR: 3200 (NR), 1695 and 1664 (C=O) cm–1; 1H-NMR: 7.65 (m); 7.4-7.28 (m); 7.03 (t); 6.91 (s); 6.31 (d); 5.11 (d); 4.38 (d); 4.15 (m); 3.88 (m); 3.22 (d); 2.94 (m); 2.66-2.54 (m); 1.86-1.76 (m); 1.58 (d); 1.46 (d); 1.25 (d); 1.20 (d).

EXAMPLE 11

N-[1-(1-Adamantylmethyl)-2,4-dioxo-5-[2-(4-morpholino)ethyl]-2,3,4,5-tetrahydro-1H-benzodiazepin-3-yl]-N'-phenylurea Isomer 1 and Isomer 2

METHOD A

The compound of Example 9 was resolved into pure enantiomers (isomer 1 and isomer 2) by preparative HPLC (Pirkle D-DNBPGC 25×2.4 cm and dichloromethane-isopropyl alcohol 93/7 v/v as elutant.

Title compound Isomer 1 retention time tr 5.2 min, alpha D=–50.0 (CHCl$_3$).

Title compound Isomer 2 retention time tr=7.8 min, alpha D=+42.0 (CHCl$_3$).

METHOD B

Phenylisocyanate (0.049 ml) was added to a solution of intermediate 57, obtained by method A, (0.102 g) in dry acetonitrile (5 ml) and the mixture was stirred at 23° for 5 min. The solid was filtered off, washed with acetonitrile and triturated with EE-CH 1:1 to give the title compound(isomer 1) (0.094 g) as a white solid. T.l.c. (EA-CH 1:1) R$_f$=0.30, HPLC: e.e.=94%. α$_D$=–40°. M.p.: 157°–159° C.

$^1$H-NMR: 7.80 (m), 7.44-7.24 (m), 7.05 (m), 6.75 (bs), 6.21 (bd), 5.12 (d), 4.39 (d), 4.14 (m), 3.78 (m), 3.75 (m), 3.22 (d), 2.93 (m), 2.75 (m), 2.57 (m), 1.83 (m), 1.64-1.18 (m). IR: 3400 (N-H), 1699, 1668, 1641 (C=O).

EXAMPLE 12

N-[1-(1-Adamantylmethyl)-2,4-dioxo-5-[(3-hydroxy-2(R) amino)propyl]-2,3,4,5-tetrahydro-1H-1,5-benzodiazepin-3-yl]-N'-phenylurea hydrochloride The solution of the racemic intermediate 35 (0.34 g) in methanol (50) previously saturated with hydrochloric acid was stirred at 20° for 4 h; the reaction mixture was concentrated under vacuum, taken up in diethylether and crystallised from methanol/diethylether to give the racemic title compound as a white solid (0.175 g ) M.p.>240° dec. IR: 3440-2500 (NH, OH, NH3$^+$), 1697 and 1684 (C=O), cm–1; 1H-NMR: 9.20 (bs); 8.36 (bs); 8.09 (bs); 7.74 (m); 7.46 (m); 7.33 (m); 7.21 (m); 6.90 (m); 6.90 (m); 5.69 (t); 5.41 (t); 4.92 (d); 4.21 (m); 4.04-3.82 (m); 3.82-3.56 (m); 3.40 (m); 1.79 (m); 1.64-1.08 (m).

EXAMPLE 13

N-[1-(Cyclohexylmethyl)-2,4-dioxo-5-[(2-diethylamino)ethyl]-2,3,4,5-tetrahydro-1H-1,5-benzodiazepin-3-yl]-N'-phenylurea Phenyl isocyanate (0.018 ml) was added to a solution of the intermediate 39 (0.057 g) in dry acetonitrile (2 ml). The reaction mixture was stirred at 23° for 30 min, then filtered to give the title compound as a white solid (0.05 g). M.p. 186°–188°. T.l.c. DCM-MeOH 9:1, Rf0.8. IR:3400 (NH), 1699, 1666 and 1641 (C=O) cm$^{-1}$; $^1$H.

EXAMPLE 14

N-[1-(1-Adamantylmethyl)-2,4-dioxo-7-fluoro-5-[2-(4-morpholino)ethyl]-2,3,4,5-tetrahydro-1H-1,5-benzodiazepin-3-yl]-N'-phenylurea Phenyl isocyanate (0.23 ml) was added to a solution of intermediate 44 (0.091 g) in acetonitrile (4 ml) and the mixture was stirred at 23° for 30 min. The mixture was concentrated in vacuo and the residue was purified by flash chromatography (eluting with DCM) then triturated with petrol to give the title compound (0.074 g) as a white solid. T.l.c. CH-EA (1:1) $R_f$ 0.37. IR (nujol): 3327 (NH), 1695-1660 (CO) cm$^{-1}$.

The compound of Example 14 was separated into its enantiomers(ISOMER 1 and ISOMER 2) by chiral HPLC using a (Pirkle D-DNBPGC5 column (25cm×2cm id), flow rate 1.0 ml/min., at 235 nm (UV detector), and eluting with DCM-IPA 93:7 v/v isomer 1 (0.048 g) as a white solid, HPLC: retention time 44 min., enantiomeric excess 100%. IR (nujol): 3327 (NH), 1695-1660 (CO) cm$^{-1}$.

isomer 2 (0.045 g) as a white solid HPLC: retention time 6.0 min., enantiomeric excess 96%. αD=+31.3. IR (nujol): 3327 (NH), 1695-1660 (CO) cm$^{-1}$.

EXAMPLE 15

N-[1-(3-methyl-1-butyl)-2,4-dioxo-5-[2-(4-morpholino)ethyl]-2,3,4,5-tetrahydro-1H-benzodiazepin-3-yl]-N'-(4-chlorophenyl)urea 4-Chlorophenyl isocyanate (0.019 ml) was added to a solution of intermediate 47 (0.05 g) in acetonitrile (2 ml). The reaction mixture was stirred at 23° for 30 min, then the solvents were removed in vacuo. The residue was triturated with diethyl ether to give the title compound as a white solid (0.046 g). M.p 210°–2° C. T.l.c. EA-MeOH (95:5), $R_f$ 0.53. IR: 1693-1641 (C=O) cm$^{-1}$;

EXAMPLE 16

N-[2,4-Dioxo-1-(3-methyl-1-butyl)-5-[2-(4-morpholino)ethyl]-2,3,4,5-tetrahydro-1H-1,5-benzodiazepin-3-yl]-N'-(4-trifluoromethyl)phenylurea 4-Trifluoromethylphenyl isocyanate (0.021 ml), was added to a solution of intermediate 47 (0.090 g) in dry acetonitrile (2 mL). The solid was filtered off, washed with diethyle to give the title compound(0.06 g) as a white solid. T.l.c. (EA/MeOH 19:1) $R_f$=0.65, M.p.: 208°–210°.

EXAMPLE 17

N-[2,4-Dioxo-1-[2-(hexamethyleneimino)ethyl]-5-phenyl -2,3,4,5-tetrahydro-1H-benzodiazepin-3-yl]-N'-(3-tolyl)urea 3-Tolyl isocyanate (0.040 ml) was added to a solution of intermediate 50 (0.154 g) in acetonitrile (7 ml). The reaction mixture was stirred at 23° for 10 min, then the solid was filtered off and oven dried to give the title compound as a white solid(0.130 g). M.p 120°–1°. T.l.c. EA-MeOH (95:5), $R_f$ 0.53. IR: 1703, 1643 (C=O) cm$^{-1}$;

EXAMPLE 18

(−)[1-(1-Adamantylmethyl)-2,4-dioxo-5-[2-(4-morpholino)ethyl]-2,3,4,5-tetrahydro-1H-1,5-benzodiazepin-3-yl]-N'-phenylurea, hydrochloride salt Example 11 isomer 1(089 g) was dissolved in methanol (15 ml), already saturated with gaseous hydrochloric acid, and the mixture was stirred at 0° for 2 h. The mixture was concentrated in vacuo and coevaporated with dichloromethane then with diethyl ether. The residue was triturated with diethyl ether to give the title compound as a white solid (0.065 g). M.p. 260°–3°. T.l.c. (EA-MeOH 9:1) Rf0.66. IR (CHCl3): 3300-2500 (NH); 1701, 1666 (C=O); 1599 (C=C) cm$^{-1}$. $^1$H-NMR: 13.2 (b); 7.56 (m); 7.45-7.20 (m); 7.06 (m); 6.44 (bd); 5.03 (d); 4.51 (m); 4.36 (d); 4.20 (m); 3.98 (m); 3.52 (m); 3.22 (d); 3.01 (m); 1.85 (m); 1.70-1.10 (m).

Pharmacy Example

| Capsules or Tablets | |
|---|---|
| | mg/dosage form |
| Active ingredient | 0.1 |
| Polyethyleneglycol | 15.0 |
| Lactose | 52.4 |
| Starch | 30.0 |
| Magnesium stearate | 0.5 |
| Silicon dioxide | 1.0 |
| Sodium Lauryl Sulphate | 1.0 |
| | 100.0 |

The active ingredient is dispersed in a suitable solvent (e.g. ethanol) together with polyethyleneglycol. The solvent is removed. The powder so obtained is blended with the other excipients. The blend can be used to fill gelatine capsules or compressed using appropriate punches. The tablets can be coated using conventional techniques and coatings.

| | |
|---|---|
| Active ingredient | 0.1 |
| Povidone | 15.4 |
| Lactose | 74.0 |
| Hydrogenated vegetable oils | 3.0 |
| Silicon dioxide | 1.0 |
| Sodium Laauryl sulphate | 1.5 |
| Crospovidone | 5.0 |
| | 100.0 |

The active ingredient is dispersed in a suitable solvent (e.g. ethanol) together with povidone. The solution is sprayed on to lactose and the solvent removed.

The powder obtained is blended with the other excipients. The blend is used to fill gelatine capsules or compressed using appropriate punches. The tablet can be coated using conventional techniques and coatings.

| Oral liquid | |
|---|---|
| Active ingredient | 70–100 micrograms/dose |
| ethanol | 5–15% |
| Sodium saccharinate | 0.1–1% |
| Propylene glycol | 10–100% |
| Purified water | qb 100% |
| Pack; plastic or glass bottle or other suitable pack | |
| Injection Formulation | |
| Active ingredient | 0.1–100 micrograms |
| Sodium phosphate | 1.50 mg/ml |
| NaOH | qs desired pH (range 3–9) |
| propylene glycol | 10–500 mg/ml |
| water for injection | qs to 0.5–10 ml |

Pack: glass (ampules) with a rubber stopper (vials, syringes) and a plastic/metal overseal (vials only) or other suitable pack. An inert gas atmosphere (for example nitrogen) may be introduced into head space of container.

CCK- Receptor Binding

The binding affinity of the compounds of the invention for the CCK-A receptor (Pancreas Assay) and CCK-B receptor (guinea pig cortex assay) was determined using the procedure of G Dal Forno et al J. Pharmacol. Exp & Ther. 261-1056–1063. The pKi values determined with representative compounds of invention were as follows:

|  | pKi | |
| --- | --- | --- |
| Compound Ex No | CCK-A | CCK-B |
| 1 | 6.17 | 8.54 |
| 2 | 5.69 | 8.17 |
| 3 | 5.48 | 8.33 |
| 4 | 5.29 | 8.10 |
| 5 | 5.08 | 8.13 |
| 6 | 5.39 | 8.80 |
| 7 | 5.49 | 8.89 |
| 8 | 4.69 | 8.44 |
| 9 | 5.69 | 9.24 |
| 10 | 5.02 | 8.98 |
| 11 (isomer 1) | 5.69 | 9.67 |
| 12 | 5.04 | 8.18 |
| 13 | 5.82 | 8.99 |
| 14 | 5.88 | 8.36 |
| 15 | 5.99 | 8.71 |
| 16 | 5.83 | 8.44 |
| 17 | 5.08 | 8.7 |

The compounds of the invention are essentially non-toxic and therapeutically useful doses. Thus for example no untoward effects were observed when the compound of Example 18 or the corresponding free base thereof (Example 11) was given orally to mice and rats at doses at which the compounds exhibit anxiolytic activity.

We claim:

1. A compound of formula (I)

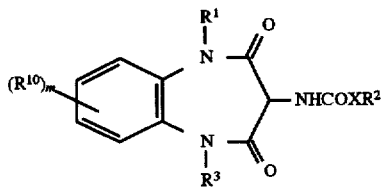

wherein:

$R^1$ represents a phenyl, $C_{3-7}$cycloalkyl, $C_{7-11}$bridged cycloalkyl or $C_{1-6}$alkyl group, which alkyl group may be substituted by a hydroxy, phenyl, $C_{1-6}$alkoxycarbonyl, $C_{3-7}$cycloalkyl, or $C_{7-11}$bridged cycloalkyl group;

$R^2$ represents a phenyl group optionally substituted by 1 or 2 substituents selected from the group consisting of halogen, $C_{1-4}$alkyl, $C_{1-4}$alkylthio, cyano, nitro, trifluoromethyl, trifluoromethoxy, $(CH_2)_nR^4$ or $O(CH_2)_pR^4$, wherein $R^4$ represents hydroxy, $C_{1-4}$alkoxy, $CO_2R^5$ or $NR^6R^7$, n is zero or 1, and p is an integer from 1 to 4;

$R^3$ represents the group $AlkNR^8R^9$;

$R^5$ represents hydrogen or $C_{1-4}$alkyl;

$R^6$ represents hydrogen or $C_{1-4}$alkyl;

$R^7$ represents hydrogen, $C_{1-4}$alkyl, $C_{1-6}$alkanoyl, or $C_{2-6}$alkyl substituted by one or more hydroxy, carboxyl and/or amino groups;

or $R^6$ and $R^7$, together with the nitrogen atom to which they are attached, represent a morpholino, 2,6-dimethylmorpholino, thiomorpholino, piperidino, 4,4-dimethylpiperidino or pyrrolidino ring;

$R^8$ and $R^9$ independently represent hydrogen, $C_{1-4}$alkyl or $C_{2-6}$alkyl substituted by one or more hydroxy, carboxyl and/or amino groups;

or $R^8$ and $R^9$, together with the nitrogen atom to which they are attached, form a morpholino, 2,6-dimethylmorpholino, hexamethyleneimino, piperidino, pyrrolidino, piperazino or N-methylpiperazino ring;

Alk represents a straight or branched $C_{2-6}$alkylene chain optionally substituted by an hydroxyl group;

$R^{10}$ represents hydrogen or a halogen atom;

m is zero, 1 or 2; and

X is oxygen or NH;

and pharmaceutically acceptable salts and/or metabolically labile esters thereof.

2. A compound as claimed in claim 1 wherein X is NH.

3. A compound as claimed in claim 1 wherein $R^1$ represents a phenyl, cyclohexylmethyl, 3-methylbutyl, or 1-adamantylmethyl group.

4. A compound as claimed in claim 1 wherein $R^1$ represents 1-adamantylmethyl.

5. A compound as claimed in claim 1 wherein $R^2$ represents a phenyl group or a phenyl group substituted by one or two groups selected from the group consisting of fluorine, chlorine, bromine, methyl, methoxy, hydroxy, trifluoromethyl, and thiomethyl.

6. A compound as claimed in claim 1 wherein $R^2$ represents phenyl, 3-methylphenyl, 4-fluorophenyl, or 4-methoxyphenyl.

7. A compound as claimed in claim 1 wherein Alk represents ethylene, propylene, or 2-hydroxymethylethylene.

8. A compound as claimed in claim 1 wherein $NR^8R^9$ represents amino, dimethylamino, morpholino, pyrrolidino, piperidino, or hexamethyleneimino.

9. A compound as claimed in claim 1 wherein $R^3$ represents morpholinoethyl, pyrrolidinoethyl, piperidinoethyl, dimethylaminoethyl, diethylaminoethyl, dimethylaminopropyl, aminopropyl, or 2-hydroxymethyl-2-aminoethyl.

10. A compound as claimed in claim 1 wherein $R^3$ represents morpholinoethyl.

11. A compound as claimed in claim 1 wherein $R^{10}$ represents hydrogen.

12. (−)[1-(1-Adamantylmethyl)]-2,4-dioxo-5-[2-(N-morpholino )-ethyl]-2,3,4,5-tetrahydro-1H-1,5-benzodiazepin-3-yl}-N'-phenylurea and physiologically acceptable salts thereof.

13. A compound which is

N[1-(1-Adamantylmethyl)-2,4-dioxo-5-[2-(4-morpholino)ethyl]-2,3,4,5-tetrahydro-1H-benzodiazepin-3-yl]-N'-phenylurea;

N-[1-(1-Adamantylmethyl)2,4-dioxo-5-[2-(4-morpholino)ethyl]-2,3,4,5 tetrahydro-1H-benzodiazepin-3-yl]-N¹-(4-fluorophenyl) urea.

N-[2,4-Dioxo-1-(3-methyl-1-butyl)-5-[2-(4-morpholino)ethyl]-2,3,4,5-tetrahydro-1H-1,5-benzodiazepin-3-yl]-N'-phenylurea;

N-[2,4-Dioxo-1-(3-methyl-1-butyl)-5-[2-(1-piperidino)ethyl]-2,3,4,5-tetrahydro-1H-1,5-benzodiazepin-3-yl]-N'-phenylurea;

N-[5-[2-(Dimethylamino)ethyl]-2,4-dioxo-1-(3-methyl-1-butyl) -2,3,4,5-tetrahydro-1H-1,5-benzodiazepin-3-yl]-N'-phenylurea;

N-[5-[2-(Dimethylamino)ethyl]-2,4-dioxo-1-(3-methyl-1-butyl) -2,3,4,5-tetrahydro-1H-1,5-benzodiazepin-3-yl]-N'-(4-methoxyphenyl)urea N-[2,4-Dioxo-1-(3-methyl-1-butyl)-5-[2-(4-morpholino)ethyl]-2,3,4,5-tetrahydro-1H-1,5-benzodiazepin-3-yl]-N'-(4-methoxyphenyl)urea;

N-[2,4-Dioxo-1-(3-methyl-1-butyl)-5-[2-(4-morpholino)ethyl]-2,3,4,5-tetrahydro-1H-1,5-benzodiazepin-3-yl]-N'-(4-hydroxyphenyl)urea;

N-[5-[2-(diethylamino)ethyl]-2,4-dioxo-1-(3-methyl-1-butyl)-]-2,3,4,5-tetrahydro-1H-benzodiazepin-3-yl]-N'-phenylurea;

N-[5-[2-diethylamino)ethyl]-2,4-dioxo-1-(3-methyl-1-butyl)-]-2,3,4,5-tetrahydro-1H-benzodiazepin-3-yl]-N'-N'-(4-fluorophenyl)urea;;

N-[(1-Adamantylmethyl)-5-[2-(dimethylamino)ethyl]-2,4-dioxo -2,3,4,5-tetrahydro-1H-1,5-benzodiazepin-3-yl]-N'-phenylurea;

N-[1-(1-Adamantyl)methyl-5-[3-(dimethylamino)propyl]-2,4-dioxo-2,3,4,5-tetrahydro-1H-1,5-benzodiazepin-3-yl]-N'-phenylurea;

N-[1-(1-Adamantylmethyl)-2,4-dioxo-5-[3-hydroxy-2(R) aminopropyl]-2,3,4,5-tetrahydro-1H-1,5-benzodiazepin-3-yl]-N'-phenylurea hydrochloride;

N-[1-(1-Cyclohexylmethyl-2,4-dioxo-5-[2-(diethylamino)ethyl]-2,3,4,5-tetrahydro-1H-benzodiazepin-1H-benzodiazepin-3-yl]-N'-phenylurea;

N-[1-(1-Adamantylmethyl)-2,4-dioxo-7-fluoro-5-[2-(4-morpholino)-ethyl]-2,3,4,5-tetrahydro-1H-1,5-benzodiazepin-3-yl]-N'-phenylurea;

N-[1-(3-methyl-1-butyl)]-2,4-dioxo-5-(2-(4-morpholino)ethyl)]-2,3,4,5-tetrahydro-1H-benzodiazepin-3-yl]-N'-(4-chlorophenyl)urea;

N-[2,4-Dioxo-1-(3-methylbut-1-yl)-5-[2-(4-morpholino)ethyl]-2,3,4,5-tetrahydro-1H-1,5-benzodiazepin-3-yl]-N'-(4-trifluoromethyl)phenylurea;

N-[1-(1-Adamantylmethyl)-2,4-dioxo-5-[2-(1-pyrrolidino)ethyl]-2,3,4,5-tetrahydro-1H-benzodiazepin-3-yl]-N'-phenylurea or N-[2,4-Dioxo-1-[2-(hexamethyleneimino)ethyl]-5-phenyl -2,3,4,5-tetrahydro-1H-benzodiazepin-3-yl]-N'-(3-tolyl)urea.

14. A process for the preparation of compounds as defined in claim 1 which comprises:

(a) reacting a compound of formula (II) wherein $R^1$, $R^3$ $R^{10}$ and m have the meanings defined in formula (I) and Y represents the group $NHCOR^{11}$ wherein $R^{11}$ is an optionally substituted phenoxy group or a 1-imidazole group.

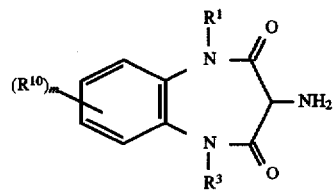

with the amine (III) $NH_2R^2$ (b) reacting a compound of formula (IV)

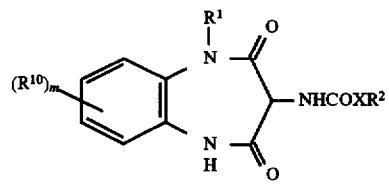

with an isocyanate of formula (V)

$$O=C=NR^2 \quad (V)$$

or an acyl chloride (VI)

$$ClCO(X)R^2 \quad (VI)$$

(c) reacting a compound of formula (XI)

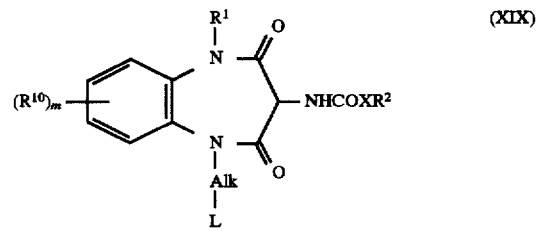

with an alkylating agent $R^8R^9$ N Alk L wherein $R^8R^9$ and Alk have the meanings defined in formula (I) and L is a leaving group.

(d) reacting a compound of formula (XIX) wherein $R^{11}$, $R^2$, $R^{10}$, m, Alk and X have the meanings defined in formula (I) and L is a leaving group

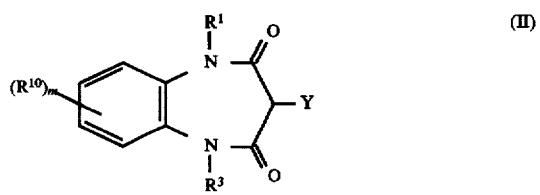

with the amine $R^8_aR^9_b$ NH wherein $R^8_a$ and $R^9_b$ have the meanings defined for the groups $R^8$ and $R^9$ respectively or $R^8_a$ and or $R^9_b$ are nitrogen protecting groups and thereafter if necessary or desired subjecting the resultant compound to one or more of the following operations:

(i) removal of one or more protecting groups.
(ii) conversion of one compound of the invention into another compound of the invention.
(iii) conversion of a compound of formula (I) into an acid addition salt thereof.

15. A pharmaceutical composition for use in the treatment of conditions where modification of the effect of gastrin and/or CCK is of therapeutic benefit, which composition comprises an effective amount of a compound as claimed in claim 1 in admixture with one or more physiologically acceptable carriers or excipients.

16. A method of treatment of a mammal, including man, for conditions where modification of the effect of gastrin and/or CCK is of therapeutic benefit comprising administration to said mammal of an effective amount of a compound as claimed in claim 1.

17. A pharmaceutical composition for use in the treatment of conditions where modification of the effect of gastrin and/or CCK is of therapeutic benefit, which composition comprises an effective amount of a compound as claimed in claim 12 in admixture with one or more physiologically acceptable carriers or excipients.

18. A method of treatment of a mammal, including man, for conditions where modification of the effect of gastrin and/or CCK is of therapeutic benefit comprising administration to said mammal of an effective amount of a compound as claimed in claim 12.

* * * * *